United States Patent
Deng et al.

(10) Patent No.: US 6,579,716 B1
(45) Date of Patent: Jun. 17, 2003

(54) BETTER EMERGENCE CHARACTERISTICS AND IMPROVED SEEDLING GROWTH UNDER LOW-LIGHT ENVIRONMENTS

(75) Inventors: Xing Wang Deng, Hamden, CT (US); Timothy McNellis, State College, PA (US); Keiko Torii, Seattle, WA (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/407,956

(22) Filed: Sep. 28, 1999

Related U.S. Application Data

(60) Provisional application No. 60/101,992, filed on Sep. 28, 1998.

(51) Int. Cl.$^7$ .......................... C12N 15/82; C12Q 1/68; C12P 19/34; C07H 21/02; C07H 21/04
(52) U.S. Cl. .......................... 435/468; 435/6; 435/91.1; 435/419; 536/23.1; 536/23.6
(58) Field of Search .......................... 435/6, 91.1, 69.1, 435/91.5, 468, 410, 419; 530/350, 370; 536/23.1, 25.3

(56) References Cited

FOREIGN PATENT DOCUMENTS

WO    WO 97/35986    10/1997

OTHER PUBLICATIONS

International Search Report for PCT/US99/22403 mailed Mar. 7, 2000 pir 60 Accession No. A44272 dated Apr. 30, 1993 U.S. Application No. 09/145,977 filed Sep. 3, 1998.
K. U. Torii et al., "Functional dissection of Arabidopsis COP1 reveals specific roles of its three structural modules in light control of seedling development", *The EMBO Journal*, vol. 17, pp. 5577–5587, (1998).
Ang et al., (1994). Regulatory hierarchy of photomorphogenic loci; allele–specific and light–dependent interaction between the Hy5 and COP1 1 loci. Plant Cell, 6, 613–628.
Deng et al., (1991). COP1): A regulatory locus involved in light–controlled development and gene expression in Arabidopsis. Genes Dev. 5, 1172–1182.
Deng et al., (1992), Genetic and phenotypic characterization of COP1 mutants of *Arabidopsis thaliana*. Plant J. 2, 83–95.
Deng et al., (1992), COP1, an Arabidopsis regulatory Gene, encodes a protein with both a zinc–binding motif and a $G_\beta$ homologous domain. Cell 71, 791–801.
Frances et al. (1997). A tomato homologue of the Arabidopsis COP1 gene exhibits a novel pattern of expression. ESOP Programme and Abstracts. European Symposium on Photomorphogenesis, Jul. 12–18, Abstract No. 489.
Kwok et al. (1996). A complement of ten essential and pleiotropic Arabidopsis genes are necessary for suppression of Photomorphogenesis in darkness. Plant Physiol. 110, 731–742.
Lupas et al. (1996). Coiled coils: new structure and new functions. TIBS, 21, 375–382.
McNellis et al. (1995) Light control of seedling morphogenetic pattern. Plant Cell 7, 1749–1761.

McNellis et al. (1994) Genetic and molecular analysis of an allelic series of COP1 mutants suggests functional roles for the multiple protein domains. Plant Cell 6, 487–500.
McNellis et al. (1994). Overexpression of Arabidopsis COP1 results in partial suppression of light mediated development: evidence for a light–inactivable repressor of Photomorphogenesis. Plant Cell 6, 1391–1400.
McNellis et al. (1996). Expression of an N–terminal fragment of COP1 confers a dominant–negative effect on light–regulated seedling development in Arabidopsis. Plant Cell, 8, 1491–1503.
Matsui et al. (1995). Arabidopsis COP1 protein specifically interacts in vitro with a cytoskeleton–associated protein, CiP1. Proc. Natl. Acad. Sci. USA, 92, 4239–4243.
Neer at al., (1994). The ancient regulatory–protein family of WD 40–repeat proteins. Nature 371, 297–300.
Staub et al. (1996). Evidence for FUS6 as a component of the nuclear localized COP9 complex in Arabidopsis. Plant Cell, 8, 2047–2056.
Tomohiko et al. (1997). Isolation and characterization of Aribidopsis COP1 homologous gene in rice. ESOP Programme and Abstracts. European Symposium on Photomorphogenesis, Jul. 12–18, 1997.
Von Arnim et al. (1993). Ring–finger motif of *Arabidopsis thaliana* COP1 defines a new class of zinc–binding domain. J. Biol. Chem. 268, 19626–19631.
Von Arnim et al. (1994). Light inactivation of Arabidopsis photomorphogenic COP1 involves a cell–specific regulation of its nucleo–cytoplasmic partitioning. Cell 79, 1035–1045.
Von Arnim et al. (1997). Genetic and developmental control of nuclear accumulation of COP1, a repressor of Photomorphogenesis in Arabidopsis. Plant Physiol. 114, 779–788.
Wei et al. (1996). The role of the COP/DET/FUS genes in light control of Arabidopsis seedling development. Plant Physiol. 112, 871–878.
Yamamoto et al. (1998). Role of a COP1 interactive protein in mediating light–regulated gene expression in Arabidopsis. Plant Cell. 10, 1083–1094.
Zhao et al. (1998). Molecular cloning and sequencing of the cDNA of COP1 gene from *Pisum sativum*. Biochemica et Biophysica Acta 1395, 326–328.
Zhou et al. (1998). COP1b, an isoform of COP1 generated by alternative splicing, has a negative effect on COP1 function in regulating light dependent seedling development in Arabidopsis. Mol Gen. Genet. 257, 387–391.

*Primary Examiner*—Sean McGarry
*Assistant Examiner*—Joe Zara
(74) *Attorney, Agent, or Firm*—Morgan, Lewis & Bockius, LLP

(57) ABSTRACT

This invention relates to seedlings which demonstrate better emergence characteristics when grown in darkness and improved seedling growth when grown under low-light levels. More specifically, the present invention relates to producing plant cells and whole plants which contain a nucleic acid sequence coding for the Coil domain as well as the sequence coding for the wildtype COP1 gene. The plants of this invention display unopened, compact leaves during seedling emergence in the darkness and reduced etiolation of seedlings grown in low-levels after emergence. The invention further relates to plant breeding methods which enable the transfer of these desirable traits to wildtype plants.

28 Claims, 13 Drawing Sheets

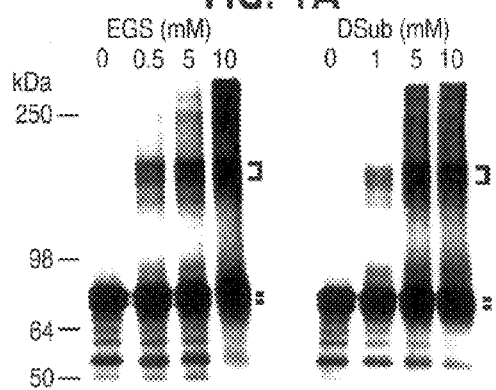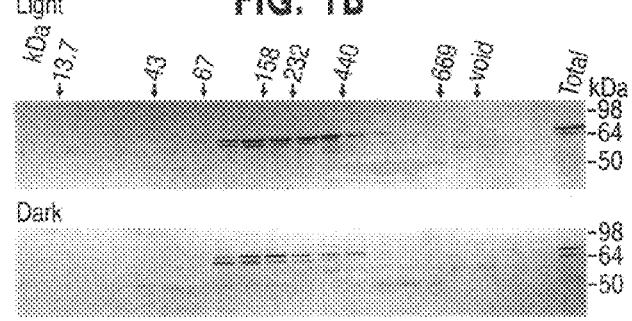

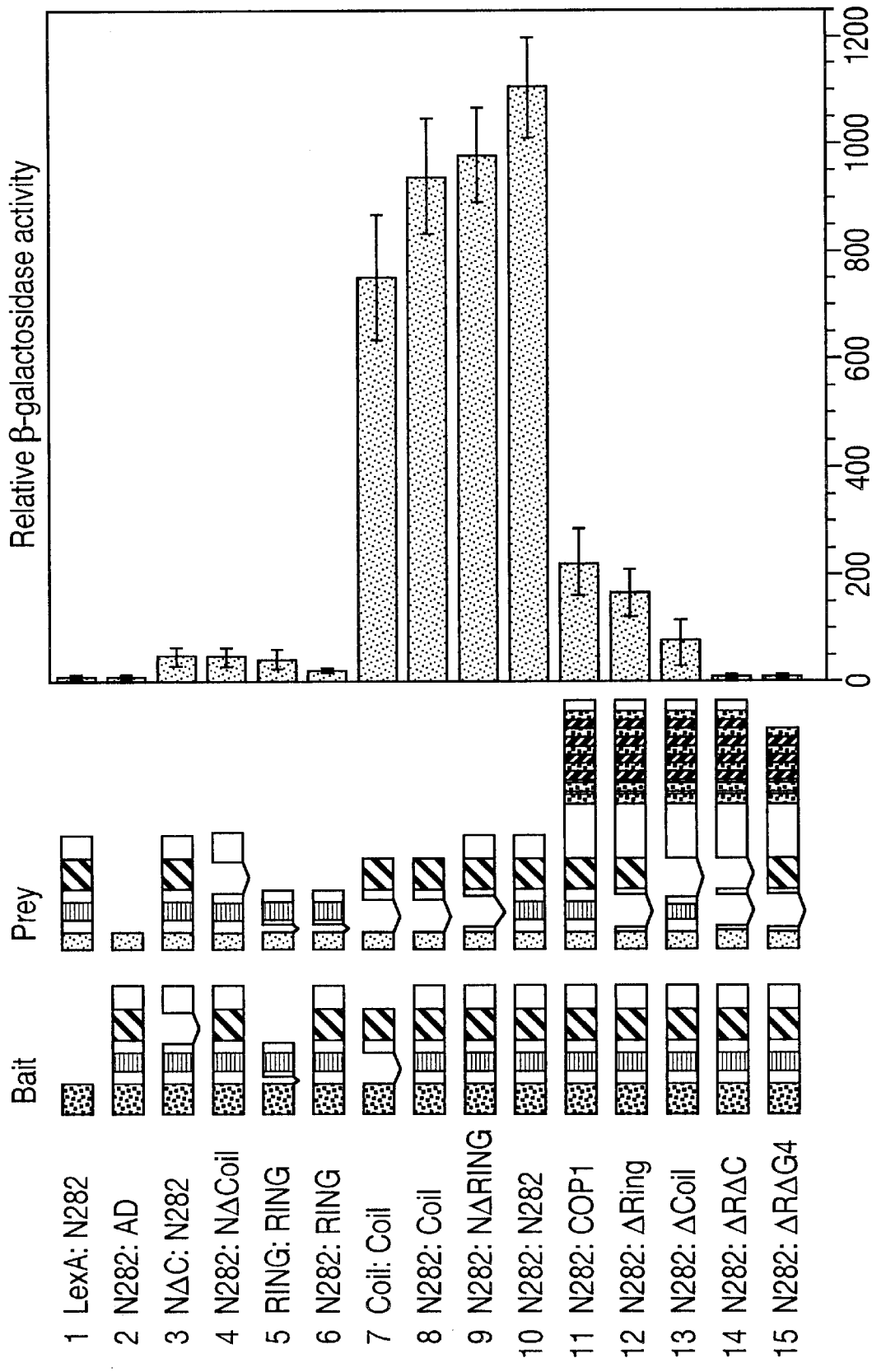

FIG. 2A
N282
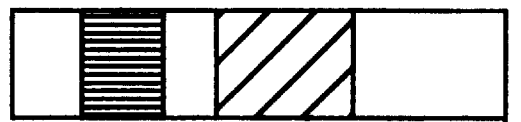
NΔRING
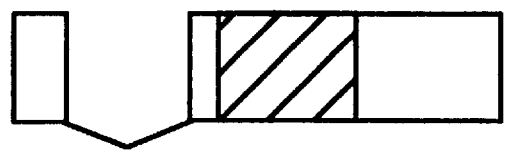
NΔCoil
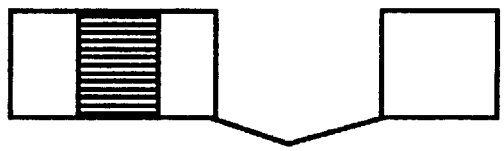

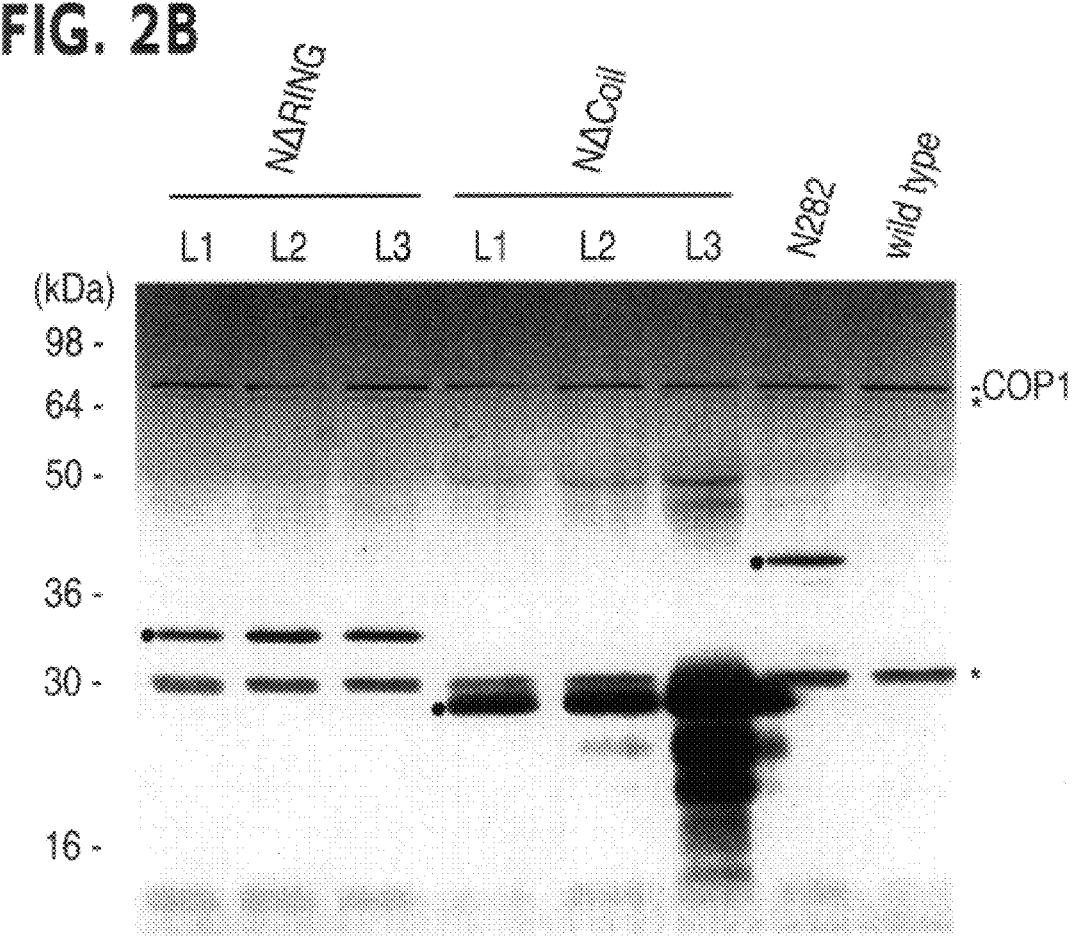

FIG. 4A GUS-ΔRING 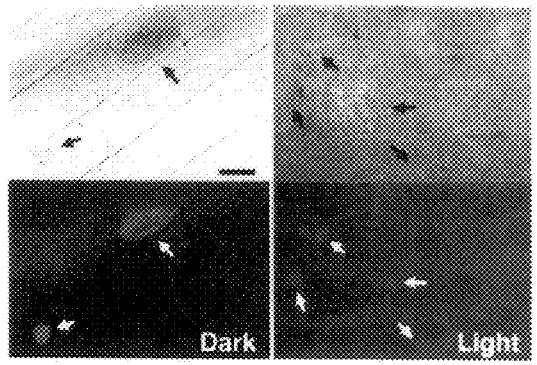 FIG. 4B GUS-ΔCoil 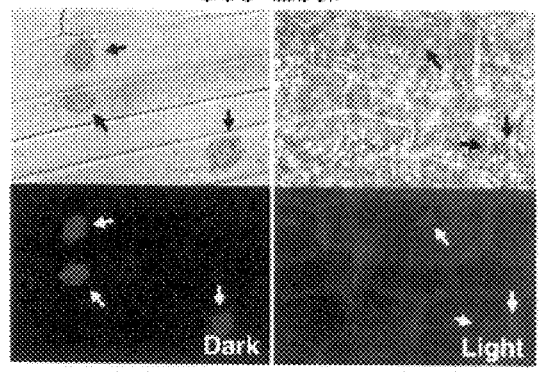
FIG. 4C GUS-ΔRΔC 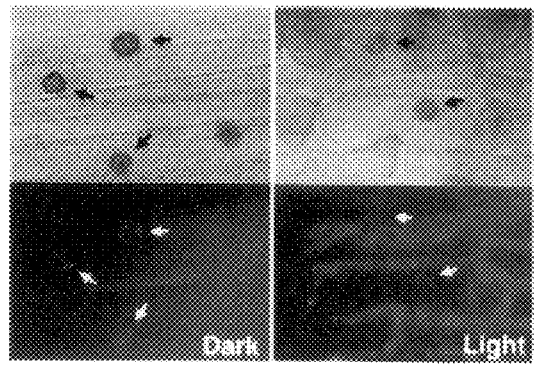 FIG. 4D GUS-ΔRΔG4 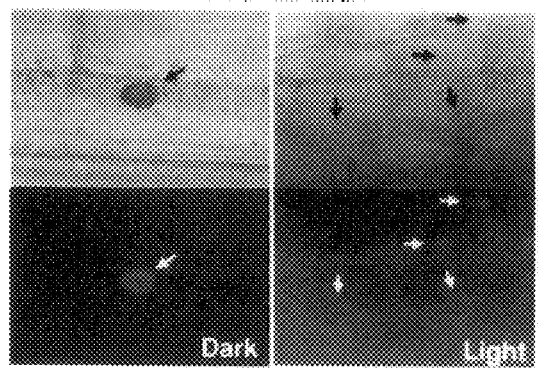

FIG. 10

```
  1   CAAAAACCAAAATCACAATCGAAGAAATCTTTTGAAAGCAAAATGGAAGAGATTTCGACGGATCCGGTTGTT
                                                      M  E  E  I  S  T  D  P  V  V

73   CCAGCGGTGAAACCTGACCCGAGAACATCTTCAGTTGGTGAAGGTGCTAATCGTCATGAAAATGACGACGGA
 11    P  A  V  K  P  D  P  R  T  S  S  V  G  E  G  A  N  R  H  E  N  D  D  G

145   GGAAGCGGCGGTTCTGAGATTGGAGCACCGGATCTGGATAAAGACTTGCTTTGTCCGATTTGTATGCAGATT
 35    G  S  G  G  S  E  I  G  A  P  D  L  D  K  D  L  L  C  P  I  C  M  Q  I

217   ATTAAAGATGCTTTCCTCACGGCTTGTGGTCATAGTTTCTGCTATATGTGTATCATCACACATCTTAGGAAC
 59    I  K  D  A  F  L  T  A  C  G  H  S  F  C  Y  M  C  I  I  T  H  L  R  N

289   AAGAGTGATTGTCCCTGTTGTAGCCAACACCTCACCAATAATCAGCTTTACCCTAATTTCTTGCTCGATAAG
 83    K  S  D  C  P  C  C  S  Q  H  L  T  N  N  Q  L  Y  P  N  F  L  L  D  K

361   CTATTGAAGAAAACTTCAGCTCGGCATGTGTCAAAAACTGCATCGCCCTTGGATCAGTTTCGGGAAGCACTA
107    L  L  K  K  T  S  A  R  H  V  S  K  T  A  S  P  L  D  Q  F  R  E  A  L

433   CAAAGGGGTTGTGATGTGTCAATTAAGGAGGTTGATAATCTTCTGACACTTCTTGCGGAAAGGAAGAGAAAA
131    Q  R  G  C  D  V  S  I  K  E  V  D  N  L  L  T  L  L  A  E  R  K  R  K

505   ATGGAACAGGAAGAAGCTGAGAGGAACATGCAGATACTTTTGGACTTTTTGCATTGTCTAAGGAAGCAAAAA
155    M  E  Q  E  E  A  E  R  N  M  Q  I  L  L  D  F  L  H  C  L  R  K  Q  K

577   GTTGATGAACTAAATGAGGTGCAAACTGATCTCCAGTATATTAAAGAAGATATAAATGCCGTTGAGAGACAT
179    V  D  E  L  N  E  V  Q  T  D  L  Q  Y  I  K  E  D  I  N  A  V  E  R  H
                                                                         A
649   AGAATAGATTTATACCGAGCTAGGGACAGATATTCTGTAAAGTTGCGGATGCTCGGAGATGATCCAAGCACA
203    R  I  D  L  Y  R  A  R  D  R  Y  S  V  K  L  R  M  L  G  D  D  P  S  T

721   AGAAATGCATGGCCACATGAGAAGAACCAGATTGGTTTCAACTCCAATTCTCTCAGCATAAGAGGAGGAAAT
227    R  N  A  W  P  H  E  K  N  Q  I  G  F  N  S  N  S  L  S  I  R  G  G  N

793   TTTGTAGGCAATTATCAAAACAAAAAGGTAGAGGGGAAGGCACAAGGAAGCTCTCATGGGCTACCAAAGAAG
251    F  V  G  N  Y  Q  N  K  K  V  E  G  K  A  Q  G  S  S  H  G  L  P  K  K

865   GATGCGCTGAGTGGGTCAGATTCG
275    D  A  L  S  G  S  D  S
```

BETTER EMERGENCE CHARACTERISTICS AND IMPROVED SEEDLING GROWTH UNDER LOW-LIGHT ENVIRONMENTS

RELATED APPLICATIONS

This application claims priority to copending provisional application No. 60/101,992, filed Sep. 28, 1998, and is incorporated herein in its entirety.

STATEMENT OF RIGHTS TO INVENTIONS MADE UNDER FEDERALLY SPONSORED RESEARCH

This invention was partially made with government support under National Institutes of Health Grant No. GM47850.

FIELD OF THE INVENTION

The present invention pertains, in general, to the production of seedlings which demonstrate better emergence characteristics and improved seedling growth when grown under low light conditions. In particular, the present invention pertains to modifying the genotypes of plant cells to include a sequence coding for the Coil domain of the COP1 protein.

BACKGROUND OF THE INVENTION

All publications and patent applications herein are incorporated by reference to the same extent as if each individual publication or patent application was specifically and individually indicated to be incorporated by reference.

Through photosynthesis, light provides the energy source for plants and, ultimately, for all living organisms. The light environment plays a crucial role in plant growth and development. Besides serving as a source of energy, light provides signals to regulate many complex developmental processes. At least three photoreceptor families—pytochromes (red and far-red light), blue light receptors, and UV light receptors—mediate these light-regulated developmental processes. Light signals perceived by specific photoreceptors are transduced via signaling components to bring about the diverse downstream physiological responses, including seed germination, stem elongation, chloroplast and leaf development, floral induction, and coordinated expression of many light-regulated nuclear- and chloroplast-encoded genes.

In response to a fluctuating environment, the nonmobile plant must be able to sense varying light signals and to optimize growth and development. Higher plants possess sophisticated photosensory and signal transduction systems to monitor the direction, quantity, and quality of the light signal and to adjust their growth and development through regulated gene expression at every stage of their life cycle, such as germination, seedling development, and flowering. These light-regulated developmental processes are collectively termed photomorphogenesis.

Plant development is a highly malleable process that is strongly influenced by environmental factors, especially light. The effects of light on plant development are especially prominent at the seedling stage (Kendrick and Kronenberg, 1994; McNellis and Deng, 1995). As compared with plants grown in light, those grown in darkness are white or yellow in color, the internodes are long, the leaves are very much reduced in size, and the root systems are poorly developed. This condition is known as etiolation. Of course, etiolated seedlings cease growth when their reserve food supply is exhausted. While the effect is less dramatic than when plants are grown in darkness, the etiolation effect also occurs under low light levels as well.

The light environment in nature is complex. Unobstructed sunlight consists of a wide continuum of photon wavelengths that is conveniently divided into three large spectral domains: UV (<400 nm), visible (400 to 700 nm) and far-red (>700 nm) light. The spectral quality, or relative photon distribution, at different wavelengths can vary greatly, depending on the location and the time of day. For example, within the canopy, the light available is essentially depleted in the visible and UV regions, and far-red light is highly represented. Furthermore, twilight normally has a higher far-red to red ratio than daylight. Although higher plants effectively utilize only visible light for photosynthesis, they have the capability to sense and respond to a much wider range of the spectrum, including UV and far-red light.

In a photochemical process such as photosynthesis, the end product depends upon the number of quanta absorbed rather than the total light energy absorbed. A single red photon has the same effect in photosynthesis as a single blue photon, for example, although the blue photon has more energy. Hence, in the recent literature it has become common to refer to the number of photons per unit area per unit time. Einsteins (for photosynthesis) or microEinsteins (for low light responses) are used. While an open field during a mid-summer day may receive as much as 2,000 microEinsteins per square meter per second, the same area in an indoor room with fluorescent lamps may only receive 50 to 100 microEinsteins per square meter per second. When the open field has its light blocked by smog, clouds or rain, it may actually register less photons per unit area per unit time than the indoor room.

In general, absence of light increases, and presence of light decreases, the rate at which the stems elongate. Thus, the features associated with etiolation ensure, under natural conditions, that the shoot is carried towards the light as rapidly as possible. Such a physiological and morphological response to the complete lack of light is critical for the growth and eventual emergence of the seedling from the position where the seed is planted in the soil or other growth media.

The etiolation process does not necessarily cease once the seedlings successfully emerge from the soil or other growth media. In many plants, there is a rhythmic night-and-day growth rate of the shoot—greater at night than during the day, provided that the temperature at night does not fall too low. Plants grown in full light have shorter and sturdier stems and somewhat thicker leaves than those grown in the shade. One result of crowding plants is a reduction in the light intensity to which they are exposed. In an effort to reach higher light levels, the shaded plants develop longer and more spindly stems than those grown under less crowded conditions. Thus, in some circumstances, the etiolation process can be viewed as a survival tactic.

However, under some conditions of low natural light, such as would result from a succession of smoggy, cloudy or rainy days or from an inability to supply high levels of artificial light in the greenhouse, etiolation can cause plant husbandry problems. For example, etiolated seedlings tend to fall over easily and to produce weaker plants which are more susceptible to pests, such as aphids and spider mites, and to other environmental challenges, such as wind or water-logged pots or fields. Under such conditions, the etiolated seedlings may develop into less vigorous adult plants, produce less reproductive structures and fewer offspring, or even perish. If a sufficient number of seedlings or plants are adversely affected by the etiolation effect, this may result in reduced production of a particular plant product on a per surface area yield basis. For example, the yield of tomato fruits on a per hectare or per acre basis may be dramatically reduced if severe seedling etiolation results in the formation of spindly tomato plants which lodge. Such lodging can reduce fruit size through decreased photosynthetic activity of the collapsed shoot, greatly increase fruit rotting through contact of the fruit with the soil, and lead to greater pest access and pest damage of the fruits. While the spindly tomato plants could be supported on trellises, stakes or cages, such rescue attempts are very labor intensive and can be prohibitively costly for large-production operations. In addition, such increased "man-handling" of the plants can also result in further plant breakage and fruit droppage.

Plant responses to light are especially evident in the young seedling, although they occur throughout the life of the plant. Early seedling development in Arabidopsis (*Arabidopsis thaliana*) provides an excellent model system to dissect the light signal transduction pathway in plants. As a typical dicotyledonous plant, Arabidopsis seedlings follow two distinct strategies of development, skotomorphogenesis in darkness or photomorphogenesis in light. Thus, Arabidopsis seedlings display contrasting developmental patterns in the presence or absence of light. In selecting for and characterizing late germinating mutants of Arabidopsis, Michelle Stopper and James J. Campanella (*Arabidopsis thaliana* Database, http://genome.www.stanford.edu/Arabidopsis) used high-intensity light conditions of approximately 450 microEinsteins per square meter per second and low-intensity light conditions of approximately 100 microEinsteins per square meter per second.

Under normal light conditions, seedlings follow photomorphogenic development characterized by inhibition of hypocotyl elongation, development of expanded cotyledons, biogenesis of chloroplasts, and expression of light-inducible genes.

In darkness, seedlings etiolate, displaying elongated hypocotyls, closed and unexpanded cotyledons, and apical hooks. Also, the light-inducible genes are repressed, and plastids develop into non-photosynthetic etioplasts in the darkness. This developmental commitment is plastic and reversible; the etiolated seedlings can dynamically respond to incoming light stimuli and initiate photomorphogenesis (for review see Chory 1993; McNellis and Deng, 1995).

The typical physiological and morphological response to growing in the dark (i.e., elongated hypocotyls, closed and unexpanded cotyledons and apical hooks) produces seedlings which are better able grow through the soil and penetrate the soil surface. Such natural seedling growth is even more important for seedlings which germinate from seeds planted at greater depths than normal. If the cotyledons were to open and expand under the soil, the increased soil resistance would impede further upward growth, requiring the seedlings to expend greater energy for continued upward growth. Such premature cotyledon expansion and increased physical resistance could result in damaged cotyledons and possibly an exhaustion of food reserves prior to seedling emergence.

As discussed above, photomorphogenic development depends on the plant being able to detect light signals. At least three families of photoreceptors, phytochromes (red and far red light), blue light receptors, and ultraviolet (UV) light receptors, are utilized to sense the different light wavelengths, and the signals transduced by these receptors coordinately regulate the transcription of specific genes.

It is not fully understood how light stimuli perceived by multiple photoreceptors are transduced and integrated to affect developmental programs. If the ability of a plant to detect light signals is impaired, such as when photoreceptors are disrupted by mutations, then a growing seedling assumes a somewhat etiolated developmental pattern. Genetic screens of Arabidopsis seedlings, based on either etiolated phenotypes under light conditions or photomorphogenic phenotypes in complete darkness, have identified a large number of the light-signal transduction components involved in controlling seedling development (for review see McNellis and Deng, 1995).

A first class of mutant seedlings with reduced light-responsiveness display characteristic long hypocotyl (hy) phenotypes. This class of mutants defines positive regulators of photomorphogenesis including photoreceptors (e.g. phyA, phyB, and hy4) and components acting downstream of specific photoreceptor (e.g. fhy1,fhy3, and red1) or multiple photoreceptors (e.g. hy5). (Chory 1992; Whitelam et al., 1993; Wagner et al., 1997). For example, mutations in phytochrome A gene (PHYA) cause reduced responsiveness to far-red light signals (Dehesh et al., 1993; Nagatani et al., 1993; Parks and Quail, 1993; Whitelam et al., 1993); mutations in phytochrome B gene (PHYB) cause reduced responsiveness to red light stimulation (Reed et al., 1993; Wester et al., 1994); mutations in a putative blue light receptor gene, HY4, cause reduced responsiveness to blue light (Ahmad and Cashmore, 1993). Symptoms of reduced light responsiveness in phyA, phyB, and hy4 mutants include long hypocotyls and reduced cotyledon expansion under certain light conditions (Koornneef et al., 1980; McNellis et al., 1994b). On the other hand, photoreceptor overexpression causes hypersensitivity to the spectral quality of light that the photoreceptor primarily absorbs. For example, overexpression of PHYB causes hypersensitivity to red light (Wagner et al., 1991; McCormac et al, 1993); overexpression of PHYA causes hypersensitivity to far-red light and red light (Boylan and Quail, 1991; McCormac et al., 1991, 1992, 1993; Whilelam et al., 1992); overexpression of the CRYPTOCHROME1 (CRY1) blue light photoreceptor encoded by the HY4 locus causes hypersensitivity to blue, UV-A, and green light (Lin et al., 1995). Because of the importance of light to plant survival, it makes sense that plants have developed multiple photoreceptors with partially overlapping functions. The photoreceptors work together to monitor light signals, and stimulation of any one photoreceptor class alone appears to be sufficient to induce many aspects of seedling photomorphogenesis (Kendrick and Kronenberg, 1994; McNellis and Deng, 1995).

Several excellent reviews deal more extensively with the photoreceptor phytochromes (Quail, 1991; Furuya, 1993; Viestra, 1993), with light regulation of gene expression (Gilmartin et al, 1990; Thompson and White, 1991; Kaufman, 1993) and with photomorphogenic mutations (Chory, 1993).

The recent molecular identification of HY5 as a bZIP transcription factor may provide a tool to bridge the light signal transduction pathway to the control of gene expression (Oyama et al., 1997).

The second class of mutants includes those that display constitutive photomorphogenesis, namely constitutive photomorphogenic (cop), de-etiolated (det) and fusca (fus) mutants (reviewed by Wei and Deng, 1996). Genetic studies indicate that their gene products function as negative regulators acting downstream of multiple photoreceptors, including phyA, phyB, and the blue-light receptor CRY1 (McNellis and Deng, 1995). While a subset of these mutants are implicated in playing a role in phytohormone signaling (Chory and Li, 1997; Kraepiel and Miginiac, 1997), ten of the pleiotropic and essential COP/DET/FUS loci are believed to be responsible for mediating the suppression of photomorphogenic seedling development in darkness (Wei and Deng, 1996).

The pleiotropic CONSTITUTIVE PHOTOMORPHOGENIC/DEETIOLATED/FUSCA (COP/DET/FUS) loci may define a group of important developmental regulators specifically involved in light control of seedling morphogenesis. Mutations at all of these loci cause seedlings to exhibit essentially all aspects of photomorphogenic development in darkness (Castle and Meinke, 1994; Miséra et al., 1994; Pepper et al., 1994; Wei et al., 1994; Kwok et al., 1996). Because all of the mutations at the pleiotropic COP/DET/FUS loci are recessive and cause constitutive photomorphogenic development regardless of the actual light conditions, the proteins encoded by these loci have been postulated to act as repressors of photomorphogenesis in the dark. Light signals absorbed by the various photoreceptors are thought to reverse the repressive activities of the COP/DET/FUS proteins and allow photomorphogenic development to proceed (for a recent review, see McNellis and Deng, 1995).

Putative null mutations at all the COP/DET/FUS loci cause adult lethality and severe physiological abnormalities during seed maturation and seedling development. This has raised concern regarding the specificity of these genes in regulating light-mediated development (Miséra et al., 1994; Castle and Meinke, 1994). It is formally possible that the pleiotropic COP/DET/FUS proteins may be ubiquitous global cellular regulators and function mainly to set up the cellular environment necessary for light regulatory cascade. Although this alternative model is also consistent with the mutant phenotypes of those genes, it suggests that their gene products are not an integral part of the light regulatory cascade.

The molecular cloning of four pleiotropic COP/DET/FUS genes, namely COP1, COP9, DET1, and FUS6 (COP11) provides an opportunity to understand the molecular mechanisms of repression of photomorphogenesis (Deng et al., 1992; Castle and Meinke, 1994; Pepper et al., 1994; Wei et al., 1994). COP9, DET1, and FUS6 encode novel α-helical rich proteins that constitutively localize in nucleus (Pepper et al., 1994; Wei et al., 1994; Chamovitz et al., 1996; Staub et al., 1996). COP9 has been found to be a part of an eight subunit protein complex consisting of COP9, FUS6 (COP11), presumably COP8, and others (Wei et al., 1994; Chamovitz et al., 1996; Wei and Deng, 1996 and 1998; Wei et al., 1998). COP1, on the other hand, appears to function as an autonomous repressor of photomorphogenesis based on previous experiments in modulating COP1 cellular activity. For instance, overexpression of full-length COP1 causes reduced light responsiveness (McNellis et al., 1994b), while overexpression of a dominant negative mutant form of COP1 results in hypersensitivity to the light and a partial de-etiolation in darkness (McNellis et al., 1996). Cell biological studies using a fusion protein of COP1 with a reporter β-glucuronidase (GUS) protein revealed the light regulated nucleocytoplasmic partitioning of COP1 may be one of the mechanisms of how light negatively regulates the repressors of photomorphogenesis (von Arnim and Deng, 1994).

Moderate overexpression of COP1 in Arabidopsis has been shown to partially suppress blue and far-red light-mediated inhibition of hypocotyl elongation and blue light-mediated cotyledon expansion (McNellis et al., 1994b). Because those effects are the only phenotype that can be detected in those transgenic plants, it was, therefore, interpreted as evidence supporting COP1's direct involvement in the light signaling cascade. However, overexpression of full-length COP1 failed to have any detectable effect on the phytochrome B-mediated red light inhibition of hypocotyl elongation (McNellis et al., 1994b), possibly due to the low levels of overexpression. In addition, if COP1 functions directly within the light regulatory cascade and acts as a light-inactivable repressor of photomorphogenic development, ideally COP1 overexpression should also affect light control of plastid development and light-regulated gene expression. Limited overexpression of the COP1 protein (four fold or less) is clearly unable to cause detectable effect on the light-regulated gene expression and plastid development (McNellis et al., 1994b). Therefore the previous overexpression studies could not critically rule out the possibility that COP1 overexpression coincidentally influenced cell elongation in the hypocotyl and cell expansion in the cotyledon under our experimental conditions through a mechanism unrelated to photomorphogenesis.

To overcome the limitations of the full-length COP1 overexpression studies, we initiated an effort to overexpress specific mutated forms of COP1 to look for possible dominant-negative effects. COP1 is a 76.2 kD protein with an N-terminal Ring-finger zinc-binding domain, followed by a putative α-helical domain, and multiple WD-40 repeats in the C-terminal half that are similar to the β subunit of trimeric G-proteins (Deng et al., 1992; McNellis et al., 1994a). The complete nucleotide and amino acid sequence of COP1 was previously provided by Deng et al. (1992b) and is available as NCBI Accession Number L24437.

Thus, COP1 encodes a protein with a novel combination of three structurally recognized domains, namely an N-terminal Zn-binding domain (hereinafter called the Ring-finger domain), a putative coiled-coil region (hereinafter referred to as the Coil or coiled-coil domain), and C-terminal WD-40 repeats (Deng et al., 1992; McNellis et al., 1994a). The 282 amino acid N-terminal fragment of COP1, including the Ring-finger and Coil domains, is referred to as 'N282'.

The Ring-finger domain comprises eight metal ligands with a consensus of C3HC4 and binds two zinc atoms in a unique tetrahedral 'cross-brace', thus forming one integrated structural unit (von Arnim and Deng, 1993; for review see Berg and Shi, 1996; Borden and Freemont, 1996; Saurin et al., 1996).

The Coil region is predicted to be an α-helical structure capable of forming a superhelix (Lupas, 1996).

The WD-40 motif is about 40 amino acids in length and contains a highly conserved tryptophan-aspartate (WD) sequence (for review see Neer et al., 1994). Proteins with Ring-finger or WD repeats are involved in a wide variety of processes, including gene repression, oncogenesis, and signal transduction (for review see Neer et al., 1994; Borden and Freemont, 1996; Saurin et al., 1996). Studies in other systems have implicated roles in protein-protein interactions for all three modules, suggesting that the pleiotropic role of COP1 may be achieved through interactions with multiple proteins. However, the specific functional roles of the COP1 modules have not been addressed.

To understand the structural implications of these structural motifs, recessive mutations of the COP1 gene were isolated based on their constitutive photomorphogenic seedling development in darkness (McNellis et al., 1994a). All of the mutant lines produced dark-grown seedlings that mimicked wild-type seedlings grown in the light. The phenotype of the dark-grown mutant seedlings included: short hypocotyls, open and enlarged cotyledons, accumulation of anthocyanin, cell-type differentiation and chloroplast-like plastid differentiation in chloroplasts. Moreover, in more prolonged dark-growth periods the mutants exhibit true leaf development that parallels that in light-grown seedlings. The four mutant alleles represent two types of mutations: three alleles (cop1-1, cop1-2 and cop1-3) have severely affected phenotypes whereas one allele (cop1-4) has a less severe phenotype. Compared to the severe alleles, the cop1-4 mutant has slightly longer hypocotyls in dark-grown seedlings and does not accumulate abnormal levels of anthocyanin. Adult light-grown plants homozygous for cop1 mutations are much smaller than wild-type (rosette diameter of about 0.5–1 cm, compared to about 5–10 cm for wild-type plants) and have much lower fertility than wild-type plants when grown under the same conditions (Deng and Quail, 1992).

The cop1-4 mutant allele produced a COP1 protein with only the N-terminal 282 amino acids, including both the zinc binding and the coiled-coil domains. The weak cop1-4 allele represents a C-to-T mutation that changes the Gln-283 CAA codon to a UAA stop codon. No wildtype size COP1 protein has been observed in the protein gel blot analysis of cop1-4 mutants, suggesting that translation through the newly created stop codon, if any, is negligible (McNellis et al., 1994a). The cop1-4 mutants are still capable of reacting to light to a certain degree. Dark-grown seedlings of cop1-4 develop short hypocotyls and expanded cotyledons (Ang and Deng, 1994). However, although the allele only produces a weak phenotypic defect in the seedling stage, it causes severe size reduction of light-grown plants and greatly reduced seed set (Deng and Quail, 1992).

Previously we reported COP1 overexpression studies using stably transformed Arabidopsis plants containing transgenes encoding the N-terminal half of COP1, which contains both the Ring-finger domain (the Zn-binding motif) and the Coil domain (the putative coiled-coil domain), but depleted of the C-terminal half of COP1, which contains the entire WD-40 repeat domain (McNellis et al., 1996). The transformed plants contained DNA coding for the full-length COP1 protein as well as additional, separate DNA which encoded the N282 fragment. Overexpression of the N-terminal 282 amino acid fragment (N282) of COP1 caused a dominant negative interference with the ability of the endogenous wildtype COP1 to suppress multiple photomorphogenic development processes, including cellular differentiation, plastid development, and gene expression. This effect of N282 overexpression seems to be specific for light-regulated development, because it has no effect on stress- and pathogen-inducible gene expression. Furthermore, the phenotype of all of the transgenic N282 lines is limited to the light control of seedling development, and little effect was detected on other developmental processes and normal adult development.

As discussed above, high-level expression of the N282 fragment caused a dominant-negative phenotype similar to that of the loss-of-function cop1 mutants. The phenotypic characteristics include hypersensitivity of hypocotyl elongation to inhibition by white, blue, red, and far-red light stimuli. In the dark, N282 expression led to pleiotropic photomorphogenic cotyledon development, including cellular differentiation, plastid development, and gene expression, although it had no significant effect on hypocotyl elongation. The results implied that the N282 COP1 fragment, which contains the Ring-finger and Coil domains, is capable of interacting with either downstream targets or with the endogenous wild-type COP1, thus interfering with normal regulatory processes. We concluded that N282 of COP1 are involved in protein-protein or protein-nucleic acid interactions that are essential for the light control of seedling development by COP1 (McNellis et al., 1996).

Work conducted using the cop1 gene of Arabidopsis has a direct bearing on the seedling growth of other plants, including plants of agronomic and horticultural importance. For example, Frances et al. (1992) have noted that a pea (*Pisum sativum*) mutant with light-independent photomorphogenesis, designated lip1, had several features in common with the deetiolated Arabidopsis mutants det1, det2 and cop1. However, the researchers also noted several important differences, including varying effects on phytochrome levels, organ-specific gene expression, plastid development and response to dark adaptation. Zhao et al. (1998) cloned and sequenced the cop1 gene from pea (NCBI Accession Number Y09579). Sequence comparison between Cop1 proteins of pea and Arabidopsis revealed that the two Cop1 proteins were highly homologous in the regions with functional domains and at the C-terminus. The two Cop1 proteins are 77.5% identical and 86.9% similar in amino acid sequences. Since pea plants display typical photomorphogenesis of the higher plants, this result demonstrates that the findings in Arabidopsis have a direct bearing on the higher plants of economic importance.

McNellis et al. (1994a) noted that the C-terminal COP1 sequence had a high degree of conservation with corresponding regions of COP1 homologs in spinach (*Spinacia olereacea*) and rice (*Oryza saliva*). The observation regarding rice was particularly interesting since the morphogenic development of monocotyledonous plants is different from that of dicotyledonous plants. For example, unlike dicotyledonous plants such as Arabidopsis and spinach, monocotyledonous plants such as rice exhibit extensive leaf development in darkness. Tsuge et al. (1997) showed that a COP1 homologue exists as a single copy gene in the rice genome and that the three structural domains are highly conserved between Arabidopsis and rice.

A homologue of the Arabidopsis COP1 gene has also been cloned from tomato (TCOP1) (Frances et al., 1997). The deduced amino acid sequence of the tomato gene shows high identity to the Arabidopsis gene particularly in the three defined structural motifs.

As discussed above, there exists a need for seedlings which demonstrate improved growth characteristics under low light conditions. While seedlings of the cop1-4 mutant of Arabidopsis display somewhat shorter hypocotyls when grown under low light conditions as compared to wildtype seedlings grown under the same conditions, these mutant seedlings become unhealthy, non-productive adult plants. These mutants fail to produce any COP1 protein.

Wildtype plants transformed with the N282 fragment of COP1 display a seedling phenotype when grown under low-light conditions which is characterized by shorter hypocotyls when compared to wildtype seedlings grown under the same low light conditions (McNellis et al., 1996). However, as detailed herein and by McNellis et al. (1996), N282-transformed plants have the distinct disadvantage of also displaying abnormal cotyledon growth and expansion when grown in the dark. This aspect of the N282-transformed plants would have detrimental effects on upward seedling growth and seedling emergence, as discussed previously. Thus, there remains a need for seedlings which display normal or near-normal emergence characteristics under dark conditions and reduced seedling etiolation under low light conditions. Prior to this invention, such plants had not been realized.

This invention involves the functional dissection of COP1 domains, by utilizing a combination of reverse-genetic, biochemical, and cell biological approaches. Our discovery reveals the distinct but overlapping functions of COP1 domains in the light control of seedling development and provides a structural basis for COP1 as a molecular switch.

Our data suggests that COP1 acts primarily as a homodimer, and likely dimerizes through the coiled-coil domain. The present invention relies on the unexpected discovery that the Ring-finger and the coiled-coil domains can function independently as light-responsive modules mediating the light controlled nucleocytoplasmic partitioning of COP1. The C-terminal WD-40 domain functions as an autonomous repressor module since the overexpression of COP1 mutant proteins with intact WD-40 repeats are able to suppress photomorphogenic development. This WD-40 domain-mediated repression can be at least in part accounted for by COP1's direct interaction with and negative regulation of HY5, a bZIP transcription factor that positively regulates photomorphogenesis. However, COP1 self-association is a prerequisite for the observed interaction of the COP1 WD-40 repeats with HY5. This work thus provides a structural basis of COP1 as a molecular switch.

Using the discovery of this invention, one skilled in the art can produce plants which demonstrate better emergence characteristics combined with improved seedling growth under low-light conditions.

SUMMARY OF THE INVENTION

This invention comprises methods of altering the emergence of seedlings under extremely low light or darkness conditions and the subsequent growth of the seedlings under low light conditions. More specifically, this invention provides plants with the following physiological and morphological characteristics: 1) the seedling phenotype displayed by the plants under extremely low light conditions or in complete darkness is characterized by a lack of leaf expansion similar to that of wildtype seedlings under the same conditions; and 2) the seedling phenotype displayed by the plants under low light conditions is characterized by shorter hypocotyls when compared to wildtype seedlings grown under the same low light conditions. Even more specifically, this invention is directed to altering the emergence characteristics of seedlings in the dark and the subsequent post-emergent growth of seedlings under low light conditions by introducing a nucleotide sequence coding for the Coil domain amino acids of the COP1 gene.

This invention provides plant cells which comprise a COP1 gene and, separately, a nucleotide sequence coding for the Coil domain the COP1 gene. Thus, the plant cells provided by this invention produce both the Coil domain protein and the wildtype COP1 protein. This invention also provides plants produced from the plant cells of this invention.

The invention also encompasses transforming plants with a nucleotide sequence for COP1 wherein the WD-40 and Ring-finger domains have been disabled. There are a number of ways in which the Ring-finger and WD40 repeats can be effectively disabled in a manner that will reduce or eliminate their expressivity and function. Thus, this invention provides plant cells comprising a COP1 gene and, separately, a nucleotide sequence coding for the Coil domain of the COP1 gene, wherein the plant cell does not have a separate expressible nucleotide sequence coding for either the Ring-finger domain of the COP1 gene or for the WD-40 domain of the COP1 gene associated with said Coil domain nucleotide sequence.

This invention provides a plant comprising a nucleotide sequence coding for the Coil domain of the COP1 gene, wherein the seedling phenotype displayed by the plant during emergence is characterized by unopened leaves and subsequent seedling growth under low light conditions after emergence is characterized by shorter hypocotyls when compared to wildtype seedlings grown under the same low light conditions. The adult plant produced by the methods of this invention have approximately the same shoot size and seed set as the wildtype adult plant grown under the same conditions.

This invention also provides isolated DNA molecules encoding the Coil domain of COP1.

This invention further provides vectors comprising isolated DNA molecules encoding the Coil domain of COP1. This invention further provides such vectors which also include a promoter operably linked to the isolated DNA sequence.

This invention also provides host cells transformed with such vectors, wherein the host cells are prokaryotic cells, fungal cells or photosynthetic eukaryotic cells. Thus, this invention provides transgenic procaryotic, fungal or photosynthetic eukaryotic organism wherein the DNA sequence coding for the Coil domain protein is incorporated into the genomic DNA of the organism thereby producing transgenic organisms which produce Coil domain protein. More specifically, the transformed photosynthetic eukaryotic host cells provided by this invention include both monocotyledonous and dicotyledonous plants. Even more specifically, the transformed monocotyledonous and dicotyledonous plants provided by this invention include Arabidopsis, spinach, tomato, pea and rice.

This invention includes plants regenerated from the transformed plant cells as well as the progeny of such transformed plants, wherein the progeny also produce Coil domain protein.

This invention further provides methods of modifying the normal function of the endogenous wildtype COP1 gene, wherein the methods comprise: 1) preparing vectors comprising an isolated DNA sequence encoding the amino acids for the Coil domain of COP1; and 2) inserting the vectors into cells selected from the group consisting of prokaryotic cells, fungal cells and photosynthetic eukaryotic cells to produce transformed cells. The methods of this invention further provide for regenerating transformed plants from the transformed photosynthetic eukaryotic cells. The methods of this invention even further provide for the production of transformed progeny from the transformed regenerated plants. Furthermore, this invention further provides methods of sexually crossing the regenerated transformed plants with other plants; harvesting the resultant seed; growing seedlings from the resultant seed under extremely low light levels and selecting those that have little or no leaf expansion; and growing the selected seedlings from step c under low light levels and selecting transformed seedlings which have shorter hypocotyls than wildtype seedlings grown under the same low light conditions.

This invention also provides methods of producing transformed seedlings which have modified phenotypes during seedling emergence in darkness and when grown as seedlings under low light conditions, wherein the methods comprise: 1) preparing vectors comprising an isolated DNA sequence encoding the amino acids for the Coil domain of COP1; 2) inserting the vectors into plant cells; 3) producing viable transformed parental plants from the transformed plant cells; and 4) growing transformed seedlings from the seed produced on the viable transformed parental plants. Following the procedures outlined herein, one of ordinary skill in the plant breeding art can produce modified seedling phenotypes characterized by transformed seedlings having substantially unopened, compact, wildtype leaves during seedling emergence in the darkness and reduced etiolation of transformed seedlings under low-light levels when compared to non-transformed, wildtype seedlings grown under the same low light conditions. The methods of this invention also provide modified seedling phenotypes characterized by transformed seedlings having substantially wildtype leaf development during seedling emergence in the darkness and shorter, more vigorous stems and greener, more developed leaves of transformed seedlings when compared to non-transformed, wildtype seedlings grown under the same low light condition.

This invention also provides methods of growing crops wherein the crop includes one or more plants which contain a DNA sequence coding for the Coil domain protein and which also contain the indigenous wildtype COP1 gene. The plants with the Coil domain used in a crop include regenerated transformed plants, progeny of regenerated transformed plants, or plants produced by sexually crossing a transformed plant with a non-transformed plant.

One skilled in the art can easily make any necessary adjustments in accordance with the necessities of the particular situation.

Further objects and advantages of the present invention will be clear from the description that follows.

BRIEF DESCRIPTION OF THE DRAWINGS

FIG. 1. COP1 dimerizes in vitro and in vivo through the Coil domain.

Figure 3A:
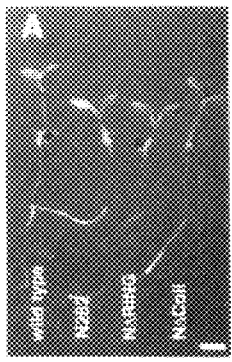
Figure 3B:
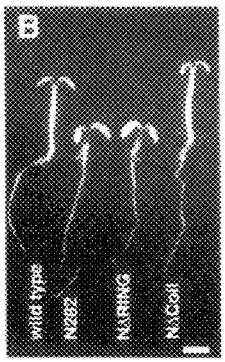
Figure 3C:
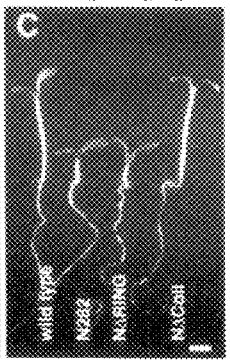
Figure 3D:
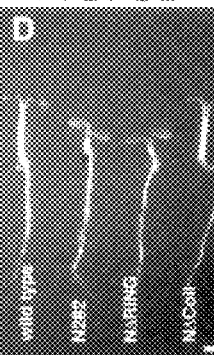

(A) In vitro cross-linking analysis of COP1. The oligomeric nature of radiolabelled flag-COP1 (indicated by bars at the right side-of each panel) was analyzed by using chemical cross-linker EGS and Dsub. Brackets at the right side of each panel indicate the positions of cross-linked products that corresponds to dimers. In vitro translated flag-COP1 yielded two bands with close molecular masses, the lower of which may due to inappropriate translation started from an endogenous methionine of COP1.

(B) The gel-filtration profiles of the COP1 protein extracted from wild-type seedlings grown under continuous white light or in darkness for six days. The proteins in the fractions were separated by SDS-PAGE and examined by protein gel immunoblot. The molecular mass (in kilodaltons) estimated by protein standards are listed above the appropriate fractions. For experimental details, see Materials and Methods.

(C) Delimitation of COP1 self-association domain utilizing the yeast two-hybrid system. For baits (Bait), COP1 domain fragments were fused with the LexA DNA binding domain (LexA). For preys (Prey), the COP1 domain fragments were fused with the synthetic transcription activation domain (AD). Numbers and names at the left indicate a pairwise combination of bait and prey constructs in each row. The graph at the right indicates the relative LacZ reporter activity in yeast cells corresponding to combinations of bait and prey constructs presented in each row. For each pairwise combination, at least 8 individual transformants were used to measure the LacZ activity. Error bars represent standard deviation. Combination 1 (LexA: N282) and 2 (N282:AD) serve as negative controls.

FIG. 2. The COP1 protein N-terminal fragments used and their expression in transgenic plants.

(A) Diagrams of the constructs used for the overexpression analysis. N282 (contains both the Ring-finger and coil domains) (McNellis et al., 1996), NΔRING (lacking the Ring-finger domain, contains the Coil domain), NΔCoil (lacking the Coil domain, contains the Ring-finger domain) are shown in comparison with the locations of the Ring-finger (RING) and Coil (Coil) highlighted. Note: aa=amino acids.

(B) Protein gel blot analysis of three representative NΔRING and NΔCoil transgenic lines are compared with the wild type and N282 transgenic line (L2: McNellis et al., 1996). Total proteins of approx. 12.5 $\mu$g were loaded on each lane. Protein blots were probed with anti-COP1 antibodies. Overexpressed N282, NΔRING, and NΔCoil protein bands are marked with dots. Protein bands corresponding to the endogenous COP1 and a non-specific reaction band at 30 kDa are marked with asterisks at the right side of the gel. Molecular mass markers (in kilodaltons) are indicated at the left.

FIG. 3. Phenotypic comparison of N282, NΔRING, and NΔCoil transgenic seedlings.

(A–E) Morphogenetic comparison of 6-day-old seedlings. Seedlings were grown (A) under continuous white light (50 $\mu$mole m$^{-2}$ sec$^{-1}$), (B) under continuous far-red light, (C) under continuous red light (40 $\mu$mole m$^{-2}$ sec$^{-1}$), (D) under continuous blue light (40 $\mu$mole m$^{-2}$ sec$^{-1}$), and (E) in complete darkness. In each panel, wild type (Columbia), N282 (L2), NΔRING (L2) and NΔCoil (L3) are shown from left to right. The scale bars represent 1 mm.

(F–J) Chloroplast autofluorescence from the roots (approx. 5 mm below the junction of the hypocotyl) of 6-day-old seedlings. (F) wild type (Columbia), (G) cop1-4, (H) N282 (L2), (I) NΔRING (L2), and (J) NΔCoil (L3). Seedlings were grown under continuous white light conditions (25 $\mu$mole m$^{-2}$ sec$^{-1}$).

FIG. 4. Representative cellular GUS staining patterns in hypocotyls of transgenic Arabidopsis. Five-day-old seedlings transgenic for (A) GUS-ΔRING, (B) GUS-_ΔCoil, (C) GUS-ΔRΔC, and (D) GUS-ΔRΔG4 were grown in complete darkness (left panels) or under high-intensity continuous white light (150 $\mu$mole m$^{31\ 2}$ sec$^{-1}$; right panels). They were stained for GUS activity without prior fixation and whole mounted in the presence of DAPI. For both GUS cytochemical staining (top panels) and DAPI staining (bottom panels), the location of representative nuclei are indicated by arrows. The scale bar in panel A represents 10 $\mu$m and applies to all panels.

FIG. 5. The COP1 domain-deletion constructs designed to analyze the in vivo function of the COP1 C-terminus and their expression in transgenic plants.

(A) Diagrams of ΔRING, ΔCoil, ΔRΔC and ΔRΔG4 in comparison to the full-length COP1 protein. Positions of putative nuclear localization signals (NLS) are indicated by ++. This set of COP1 mutants was also used for GUS fusions (GUS-ΔRING, GUS-ΔCoil, GUS-ΔRΔC, and GUS-ΔRΔG4, respectively) in subcellular localization studies (FIG. 4) and phenotypic studies. aa, amino acids.

(B) Protein gel blot analysis of the transgenic Arabidopsis expressing COP1 domain-deletion fragments that retain the intact C-terminus. Two representative transgenic lines for ΔRING, ΔCoil, ΔRΔC, and ΔRΔG4 are compared with the wild type Columbia. Total proteins of approx. 12.5 μg were loaded on each lane. Protein blots were probed with anti-COP1 antibodies. Overexpressed ΔRING, ΔCoil, ΔRΔC, and ΔRΔG4 protein bands are marked with dots. Protein bands corresponding to the endogenous COP1 and a non-specific reactions are marked with a bar or asterisks respectively at the right side of the gel. Molecular mass markers (in kilodaltons) are indicated at the left.

Figure 5A:
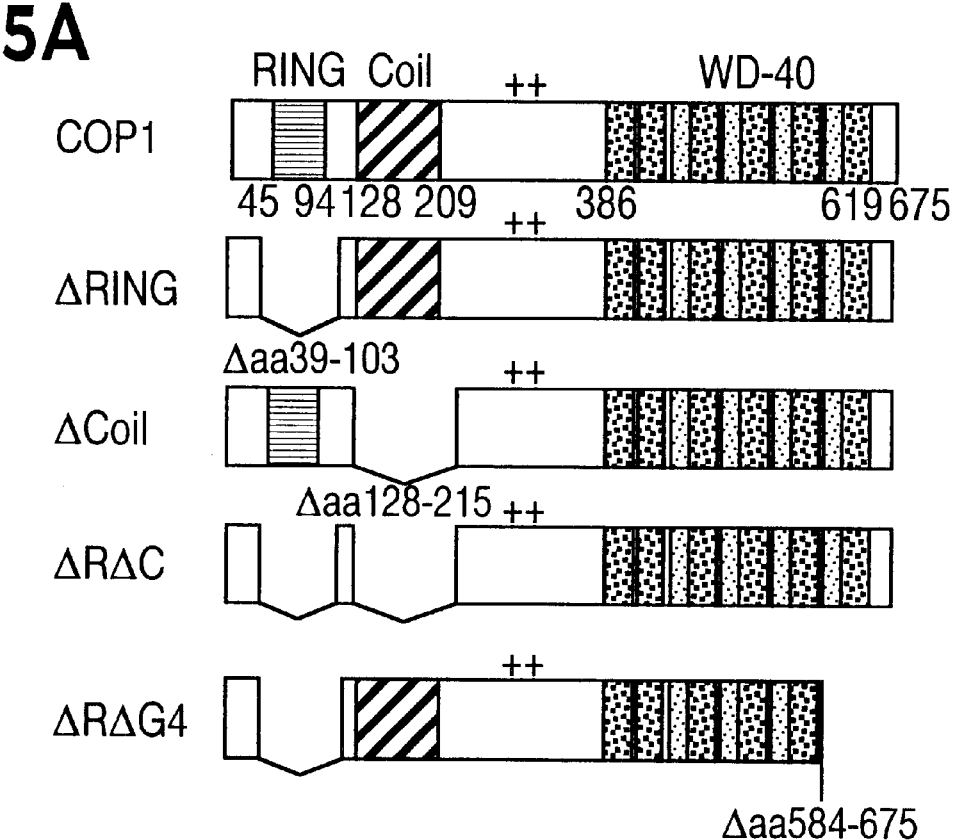
Figure 5B:
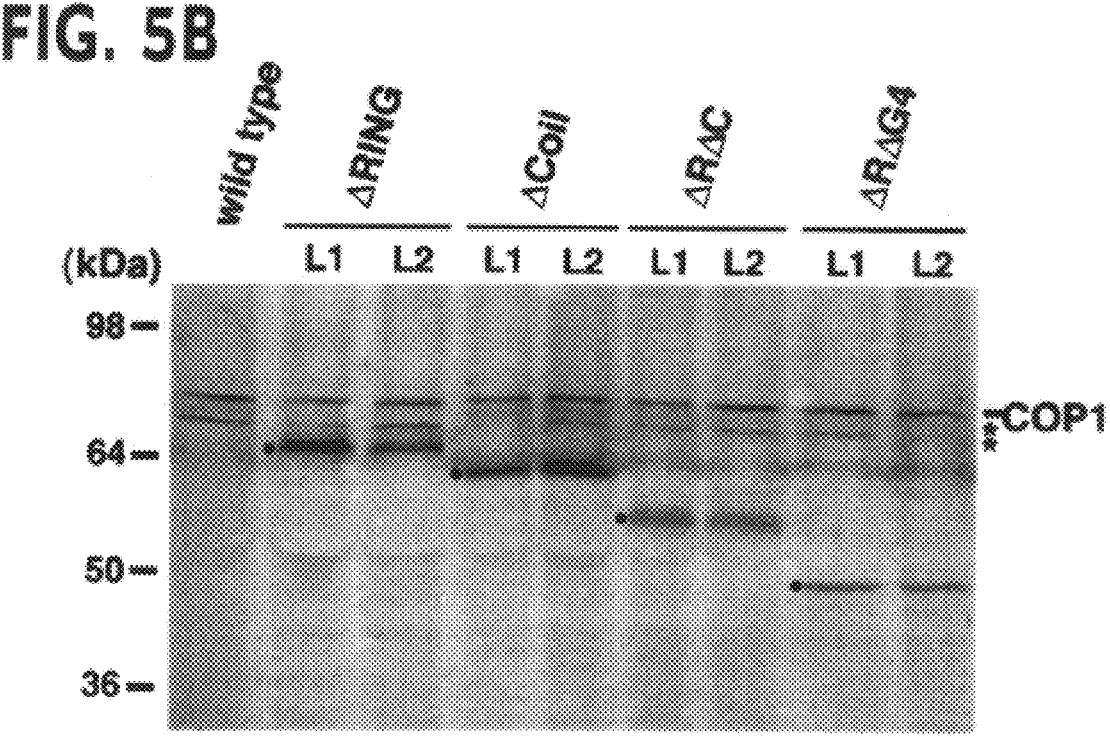
Figure 6A:
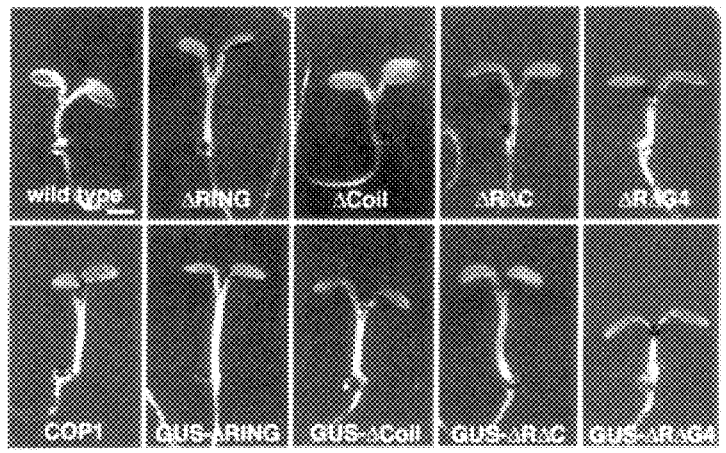
Figure 6B:
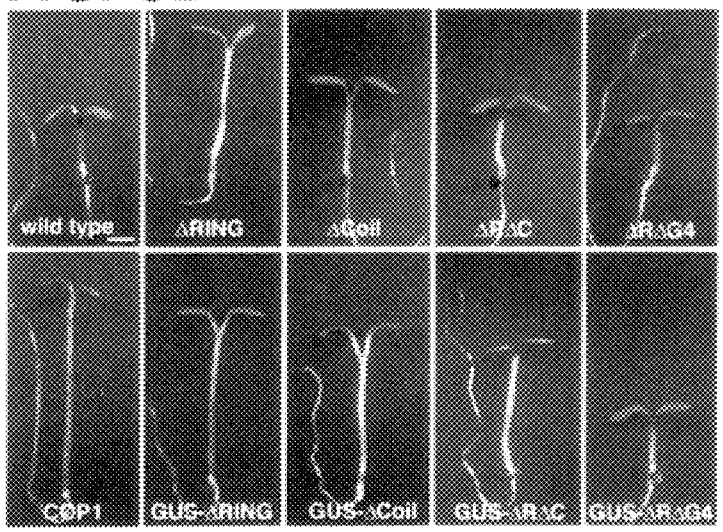
Figure 6C:
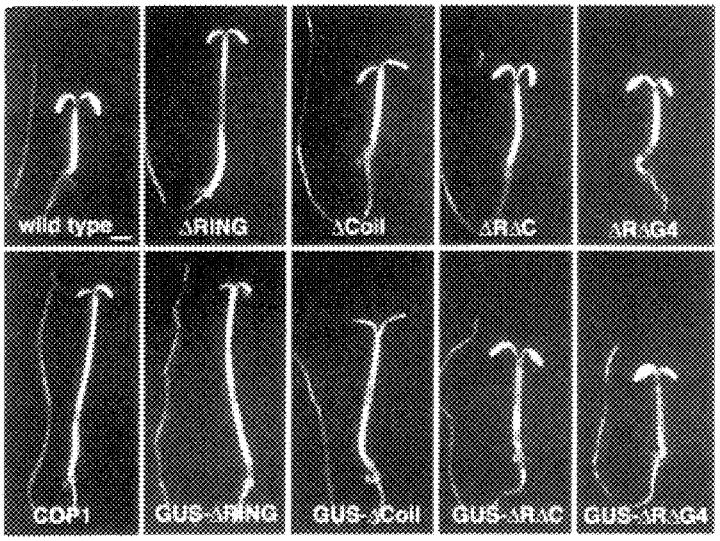

FIG. 6. Morphogenetic comparison of 6-day-old wild-type and transgenic seedlings expressing COP1 domain-deletion fragments and their GUS fusion shown in FIG. 5. Seedlings of wild type (ecotype Columbia) and transgenic Arabidopsis that overexpress a full-length COP1 (COP1; McNellis et al., 1994b), ΔRING, ΔCoil, ΔRΔC, ΔRΔG4, GUS-ΔRING, GUS-_ΔCoil, GUS-ΔRΔC, and GUS-ΔRΔG4 were grown under (A) continuous white light conditions (25 μmole m$^{-2}$ sec$^{-1}$), (B) continuous blue light conditions (12.5 μmole m$^{-2}$ sec$^{-1}$), and (C) continuous far-red light conditions. All seedlings in each panel were at the same magnifications. The scale bars represent 1 mm and all seedlings shown in one panel were taken under the same magnification.

Figure 7C:
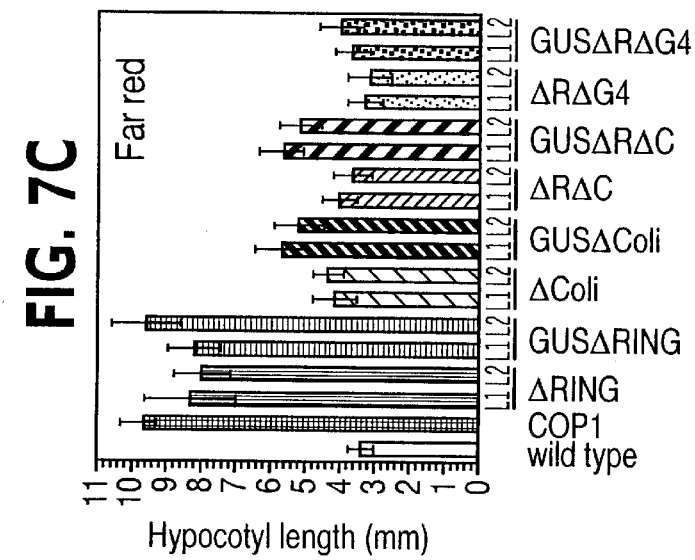
Figure 7B:
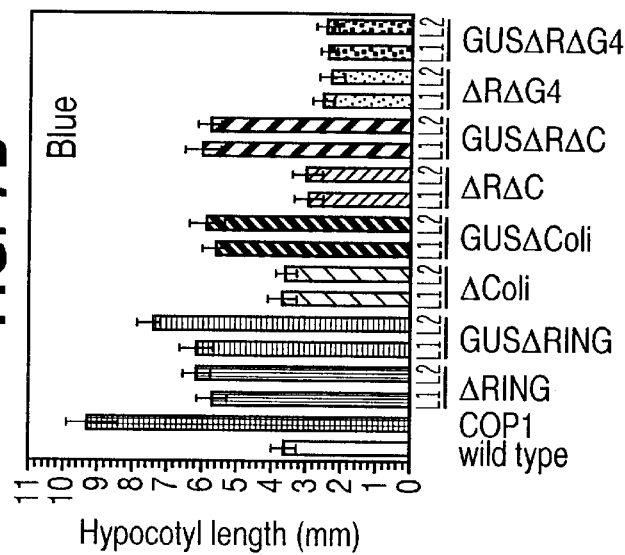
Figure 7A:
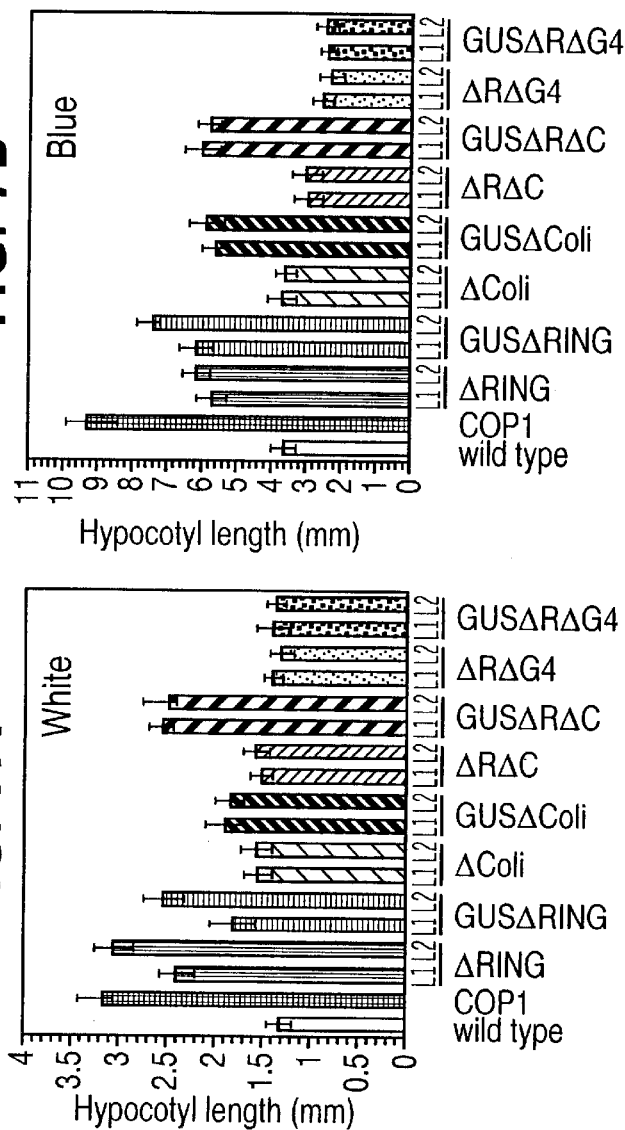

FIG. 7. Comparison of the hypocotyl lengths of wild-type and transgenic Arabidopsis seedlings that overexpress full-length COP1, and COP1 domain-deletion overexpressors. Seedlings of wild type Columbia, COP1 overexpressors, and two representative lines for ΔRING, ΔCoil, ΔRΔC, ΔRΔG4, GUS-ΔRING, GUS-ΔCoil, GUS-ΔRΔC, and GUS-ΔRΔG4 overexpressors were grown under (A) continuous white light, (B) continuous blue light, and (C) continuous far-red light conditions as shown in FIG. 6 for six days. The hypocotyls of at least 20 seedlings were measured for each line, and the means are shown on the chart. Error bars represent standard deviations.

Figure 8:
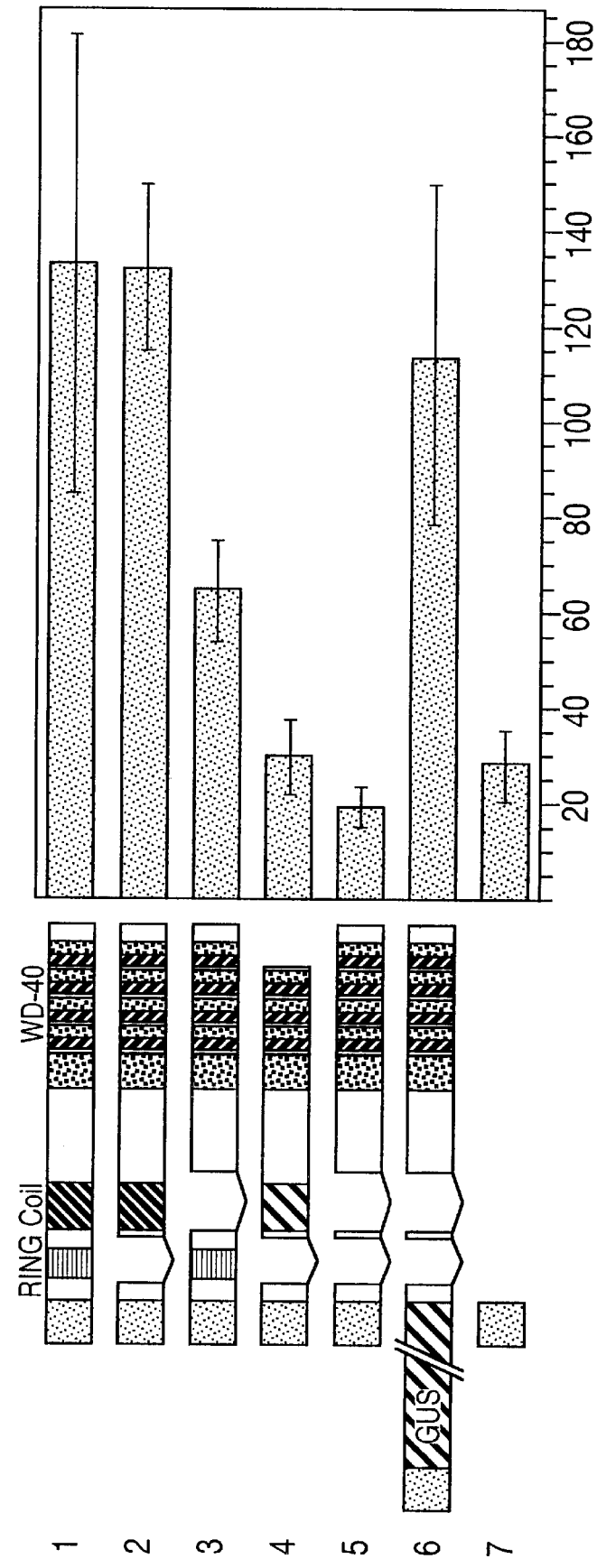

FIG. 8. Interaction between HY5 and COP1 domain-deletion mutant forms in the yeast two-hybrid system. Numbers at the left indicate a pairwise combination of the bait, LexA-HY5 (not shown), with the different prey constructs: 1, AD-COP1; 2, AD-ΔRING; 3, AD-ΔCoil; 4, AD-ΔRΔG4; 5, AD-ΔRΔC; 6, AD-GUS-ΔRΔC; and 7, AD only. Combination 7 represents a negative control. The bar graph at the right shows the relative LacZ activity of the pairwise combinations in corresponding rows. For each pairwise combination, 10 individual transformants were used to measure relative LacZ activity. Error bars represent standard deviations.

Figure 9:
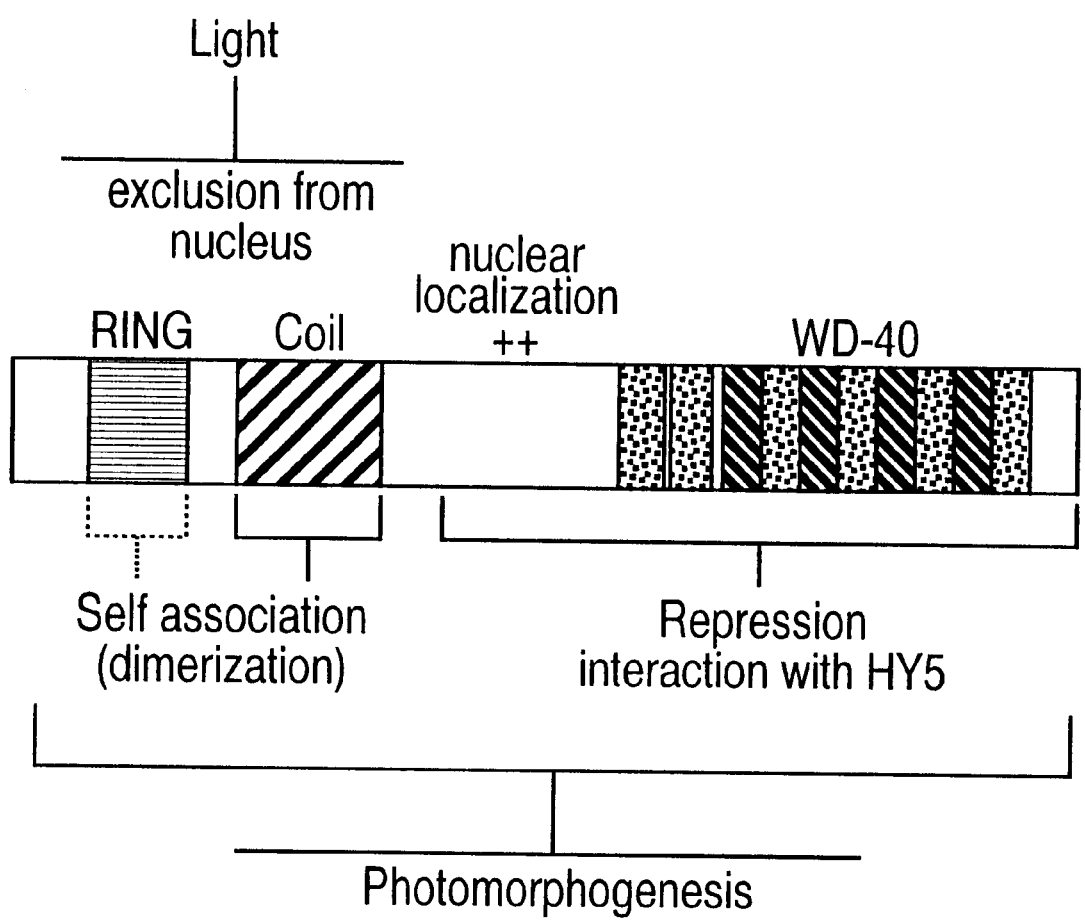

FIG. 9. Working model for COP1 domain functions in the light control of Arabidopsis seedling development. The COP1 NLS locates between the Coil and the WD-40 repeat domains. Light signals perceived by multiple photoreceptors are transduced through signaling intermediate(s) that diminish COP1 nuclear accumulation acting through both the Ring-finger and the Coil domain. A combination of the Ring-finger and the Coil domains are necessary for COP1 self-association which is a prerequisite for in vivo repressive activity of COP1. HY5 is one of the target transcription factors whose activity is inhibited by COP1.

FIG. 10. The Nucleotide Sequence (SEQ ID NO:1) and Amino Acid Sequence (SEQ ID NO:2) of N282 Isolated from the cop1-4 Mutant. The two underlined sequences represent the Ring-finger and coiled-coil homology domains, respectively. The Nucleotide Sequence (SEQ ID NO:3) and Amino Acid Sequence (SEQ ID NO:4) of the Coil domain are set forth as the last underlined portion of the N282 sequence in FIG. 10.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Overview of the Invention

As discussed above, our previous work demonstrated that expression of N282 caused a dominant-negative phenotype in both light- and dark-grown seedlings. The expression of N282 interfered with the ability of the endogenous COP1 protein to repress photomorphogenesis and resulted in increased seedling sensitivity to a variety of light signals and partial de-etiolation in total darkness. The fact that the level of wildtype COP1 protein accumulation in the N282 transgenic seedlings did not appear to be reduced as a proportion of total protein clearly ruled out the possibility that cosuppression of the endogenous wildtype COP1 gene may be responsible for the observed phenotype. These phenotypic characteristics not only confirmed a specific involvement of COP1 in the light regulatory cascade, but also allowed novel insights to be made about the functional roles of the structural domains residing in the N-terminal portion of the COP1 molecule.

In the present invention, we have dissected the functional roles of the three known COP1 domains in the control of Arabidopsis seedling development by light. Our results unveiled the distinct but cooperative nature of the functional modules of COP1. As summarized in FIG. 9, the Coil region is most likely the dimerization domain, while the N-terminal Ring-finger plays a supportive role in COP1 intramolecular interaction. Both the Ring-finger and the Coil domains are important for mediating the light triggered depletion of COP1 from nucleus. With proper self-association, the C-terminal WD-repeats are essential for mediating the repression of photomorphogenesis, possibly by directly interacting with and negatively regulating HY5.

As set forth above, the present invention is particularly directed to the production of plant cells, seedlings and adult plants which contain nucleic acid sequences coding for the Coil domain amino acids of the COP1 gene. We have made the unexpected discovery that a plant containing a nucleotide sequence coding for the Coil domain has certain improved agronomic/horticultural characteristics for seedling emergence in the dark and seedling growth under low light levels. Previous to our discovery, methods were not available to produce plants which combined these important traits.

Definitions

The COP1 gene of Arabidopsis consists of three domains: the WD-40 repeats, the Ring-finger domain (also called the Zn-binding motif) and the Coil domain (also called the coiled-coil domain). As stated previously, the complete Arabidopsis nucleotide and amino acid sequence of COP1 was previously provided by Deng et al. (1992b) and is available as NCBI Accession Number L24437.

As stated previously, the segment or fragment of COP1 which codes for the first 282 amino acids of COP1 is known as 'N282'. N282 only includes two of the three COP1 domains: the Ring-finger and Coil homology domains. The nucleotide sequence of N282 (SEQ ID NO:1) consists of bases 1 to 888 of COP1, with the corresponding amino acid sequence of N282 (SEQ ID NO:2) consisting of amino acid positions 1 to 282 of COP1. The sequence of N282, with the two domains underlined, is provided in FIG. 10. The nucleotide sequence of the Coil domain of N282 (SEQ ID NO:3) consists of bases 424 to 669 with the corresponding amino acid sequence (SEQ ID NO:4) consisting of amino acid positions 128 to 209.

The isolated nucleic acid molecules of the invention include the nucleic acid sequence encoded by the Coil domain (SEQ ID NO:3), as well as sequences which further contain additional non-Ring-finger sequences of N282. For example, nucleic acids particularly useful in the present invention include nucleic acid molecules coding for amino acids 1–38 and 104–282 of the N282 sequence (i.e., a nucleic acid molecule constructed from N282 which does not include the bases coding for amino acids at positions 39–103 of N282). Such nucleic acids include the sequence for the Coil domain as well as additional N282 nucleic acids which do not code for the Ring-finger domain or fragments thereof.

As used herein, Coil domain genes include the specifically identified and characterized variants herein described as well as allelic variants, conservative substitution variants and homologues that can be isolated/generated and characterized without undue experimentation following the methods outlined below. The nucleotide sequences of the Coil domains utilized in the present invention may include additional nucleotides of N282, wherein the additional nucleotides do not include the nucleotide sequences of the Ring-finger domain or fragments thereof. For the sake of convenience, all Coil domain or coiled-coil domain genes will be collectively referred to as the Coil domain genes of COP1 or Coil domain genes, or, alternatively, the Coil domain genes of COP1 of the present invention or the Coil domain genes of the present invention.

The terms "Coil domain genes of COP1" or "Coil domain genes" include all naturally occurring allelic variants of the Arabidopsis Coil domain genes that possess normal Coil domain activity as typified by the Coil domain genes of COP1. In general, allelic variants of the Coil domain protein of COP1 will have a slightly different amino acid sequence than that specifically encoded by the Coil domain of the Arabidopsis COP1 gene.

Accordingly, the invention provides an isolated nucleic acid molecule comprising a nucleotide sequence encoding the Coil domain of a COP1 gene or a fragment thereof, wherein such Coil domains can further include additional non-Ring-finger domain bases of N282. The invention also includes degenerate sequences of the DNA as well as sequences that are substantially homologous. The exemplified source of the Coil domain for the invention is Arabidopsis, although Coil domains from any source is encompassed by the invention. Thus, the invention encompasses the nucleic acids for the Coil domain of any other monocotyledonous or dicotyledonous plant species, including tomato, spinach, pea and rice. Considering the diversity of plant species in which a COP1 gene has been identified, the COP1 gene is most likely ubiquitous in the plant kingdom. Furthermore, the three domain nature of the COP1 gene also appears to be widespread in the plant kingdom.

The nucleic acid molecule or fragment thereof, may also be synthesized using methods known in the art. It is also possible to produce the molecule by genetic engineering techniques, by constructing DNA using any accepted technique, cloning the DNA in an expression vehicle and transfecting the vehicle into a cell which will express the compound. See, for example, the methods set forth in Sambrook et al., *Molecular Cloning: A Laboratory Manual*, 2nd edition, Cold Spring Harbor Laboratory Press, 1985.

It is understood that all polynucleotides encoding all or a portion of the Coil domain are also included herein, as long as they encode a polypeptide with the functional activities of the Coil domain as set forth herein. Polynucleotide sequences of the invention include DNA, cDNA, synthetic DNA and RNA sequences which encode the Coil region. Such polynucleotides also include naturally occurring, synthetic and intentionally manipulated polynucleotides. For example, such polynucleotide sequences may comprise genomic DNA which may or may not include naturally occurring introns. Moreover, such genomic DNA may be obtained in association with promoter regions or poly A sequences. As another example, portions of the mRNA sequence may be altered due to alternate RNA splicing patterns or the use of alternate promoters for RNA transcription. As yet another example, Coil domain polynucleotides may be subjected to site-directed mutagenesis.

The polynucleotides of the invention further include sequences that are degenerate as a result of the genetic code. The genetic code is said to be degenerate because more than one nucleotide triplet codes for the same amino acid. There are 20 natural amino acids, most of which are specified by more than one codon. It will be appreciated by those skilled in the art that as a result of the degeneracy of the genetic code, a multitude of nucleotide sequences, some bearing minimal nucleotide sequence homology to the nucleotide sequence of SEQ ID NO:3 may be produced as a result of this invention. Therefore, all degenerate nucleotide sequences are included in the invention as long as the amino acid sequence of the Coil domain polypeptide encoded by the nucleotide sequence is functionally unchanged or substantially similar in function. The invention specifically contemplated each and every possible variation of peptide or nucleotide sequence that could be made by selecting combinations based on the possible amino acid and codon choices made in accordance with the standard triplet genetic code as applied to the Coil domain sequences of COP1 of the invention, as exemplified by SEQ ID NO:3, and all such variations are to be considered specifically disclosed herein.

Also included in the invention are fragments (portions, segments) of the sequences disclosed herein which selectively hybridize to the sequence of the Coil domain of COP1. Selective hybridization as used herein refers to hybridization under stringent conditions (See, for example, the techniques in Maniatis et al., *Molecular Cloning: A Laboratory Manual*, Cold Spring Harbor Laboratory Press, 1989), which distinguishes related from unrelated nucleotide sequences. The active fragments of the invention, which are complementary to mRNA and the coding strand of DNA, are usually at least about 15 nucleotides, more usually at least 20 nucleotides, preferably 30 nucleotides and more preferably may be 50 nucleotides or more.

As used herein, "stringent conditions" are conditions in which hybridization yields a clear and readable hybridization signal. Stringent conditions are those that (1) employ low ionic strength and high temperature for washing, for example, 0.015 M NaCl, 0.0015 M sodium citrate, 0.1% SDS buffer at 50° C., or (2) employ during hybridization a denaturing agent such as formamide, for example, 50% formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 40° C. Another example is using 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS and 10% dextran sulfate at 40° C., with washes at 40° C. in 0.2×SSC and 0.1% SDS. A skilled artisan can readily determine and vary the stringency conditions appropriately to obtain a clear and detectable hybridization signal.

The present invention provides nucleic acid molecules encoding Coil domain proteins which hybridize with nucleic acid molecules comprising sequences complimentary to the Coil domain of COP1 under conditions of sufficient stringency to produce a clear signal. As used herein, "nucleic acid" is defined as RNA or DNA encoding Coil domain peptides, or are complimentary to nucleic acids encoding such peptides, or hybridize to such nucleic acids and remain stably bound to them under stringent conditions, or encode polypeptides sharing at least 60% sequence identity, preferably at least 70% sequence identity, and more preferably at least 80% sequence identity with the Coil domain peptide sequences.

Plants naturally contain a wildtype COP1 gene that codes for wildtype COP1 protein. Wildtype, when referring to nucleic acid sequences or protein sequences, means the genetic constitution of an organism in which a number of mutations (markers) may already exist at the start of a program of mutagenesis before further changes are introduced. Thus, the wildtype COP1 protein refers to the various forms of COP1 protein found naturally before the introduction of a nucleotide sequence coding for the Coil domain of the wildtype COP1 gene.

As used herein, the Coil domain protein refers to a protein that has the amino acid sequence encoded by the polynucleotide of the Coil domain of COP1, allelic variants thereof and conservative substitutions thereof that have Coil domain activity. The Coil domain protein of the present invention may include additional non-Ring-finger domain sequences of N282. In addition, the polypeptides of the invention include the protein encoded by the Coil domain set forth as SEQ ID NO:4, as well as polypeptides and fragments, particularly those which have the biological activity of the Coil domain and also those which have at least 70% sequence identity to the polypeptides encoded by the Coil domain of COP1 or the relevant portion, preferably at least 80% identity to the polypeptides encoded by the Coil domain of COP1, and more preferably at least 90% similarity (more preferably at least 90% identity) to the polypeptides encoded by the Coil domain of COP1 and still more preferably at least 95% similarity (still more preferably at least 95% identity) to the polypeptides encoded by the Coil domain of COP1 and also include portions of such polypeptides.

The Coil domain proteins of the present invention include the specifically identified and characterized variant herein described as well as allelic variants, conservative substitution variants and homologues that can be isolated/generated and characterized without undue experimentation following the methods outlined below.

For the sake of convenience, all Coil domain proteins or coiled-coil domain proteins will be collectively referred to as the Coil domain proteins of COP1 or the Coil domain proteins, or, alternatively, as the Coil domain proteins of COP1 of the present invention or Coil domain proteins of the present invention.

The terms "Coil domain proteins of the present invention" or "Coil domain proteins" include all naturally occurring allelic variants of the Arabidopsis Coil domain proteins that possess normal Coil domain activity as typified by the Coil domain proteins of COP1. In general, allelic variants of the Coil domain protein of COP1 will have a slightly different amino acid sequence than that specifically encoded by the Coil domain of the Arabidopsis COP1 gene.

The invention further provides substantially pure Coil domain polypeptides. The term "substantially pure" as used herein refers to Coil polypeptide which is substantially free of other proteins, lipids, carbohydrates or other materials with which it is naturally associated. One skilled in the art can purify Coil using standard techniques for protein purification (Matsumoto et al., 1997; Self et al., 1995).

The invention also provides amino acid sequences coding for isolated Arabidopsis polypeptides of the Coil domain of COP1. The polypeptides of the invention include those which differ from the exemplified Coil domains (e.g, SEQ ID NO:4) as a result of conservative variations. The terms "conservative variation" or "conservative substitution" as used herein denotes the replacement of an amino acid residue by another, biologically similar residue. Conservative variations or substitutions are not likely to change the shape of the polypeptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine, and the like. Therefore, all conservative substitutions are included in the invention as long as the Coil domain polypeptide encoded by the nucleotide sequence is functionally unchanged or similar.

As used herein, an isolated Coil protein can be a full-length Coil domain protein or any homologue of such a protein, such as a Coil protein in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycosylphosphatidyl inositol), wherein modified protein retains the physiological characteristics of natural Coil domains. A homologue of a Coil protein is a protein having an amino acid sequence that is sufficiently similar to a natural Coil protein amino acid sequence that a nucleic acid sequence encoding the homologue is capable of hybridizing under stringent conditions to (i.e., with) a nucleic acid sequence encoding the natural Coil protein amino acid sequence. Appropriate stringency requirements are discussed above.

Coil domain protein homologues can be the result of allelic variation of a natural gene encoding a Coil protein. Natural genes are also referred to as "wildtype genes." A natural, or wildtype, gene refers to the form of the gene found most often in nature. Coil domain protein homologues can be produced using techniques known in the art including, but not limited to, direct modifications to a gene encoding a protein using, for example, classic or recombinant DNA techniques to effect random or targeted mutagenesis.

Minor modifications of the Coil primary amino acid sequence may result in proteins which have substantially equivalent activity as compared to the Coil polypeptides described herein in SEQ ID NO:4. As used herein, a "functional equivalent" of the Coil protein is a protein which possesses a biological activity or immunological characteristic substantially similar to a biological activity or immunological characteristic of non-recombinant, or natural, Coil. The term "functional equivalent" is intended to include the fragments, variants, analogues, homologues, or chemical derivatives of a molecule which possess the biological activity of the Coil domain proteins of the present invention.

The term "Coil domain proteins" includes all naturally occurring allelic variants of the Arabidopsis Coil domain protein that possess normal Coil domain activity. In general, allelic variants of the Coil domain protein will have a slightly different amino acid sequence than that specifically encoded by SEQ ID NO:4 but will be able to produce the exemplified seedling phenotype under low light conditions. Allelic variants, though possessing a slightly different amino acid sequence than those recited above, will posses the ability to produce a seedling phenotype which exhibits: 1) compact, unexpanded leaves during seedling growth in extremely low light or complete darkness; and 2) shorter, more vigorous stems and greener, more developed leaves when compared to wildtype seedlings lacking a specific sequence coding for the Coil domain protein when grown under low light conditions. Typically, allelic variants of the Coil domain protein will contain conservative amino acid substitutions from the Coil domain sequences herein described or will contain a substitution of an amino acid from a corresponding position in an Coil domain homologue (an Coil domain protein isolated from an organism other than Arabidopsis, such as rice, tomato, pea or spinach).

The methods of the present invention can be used by one skilled in the art of plant breeding and plant husbandry to produce crop plants with improved characteristics for emergence and early seedling growth. As used herein, the term "crop plant" means any plant grown for any commercial purpose, including, but not limited to the following purposes: seed production, hay production, ornamental use, fruit production, berry production, vegetable production, oil production, protein production, forage production, animal grazing, golf courses, lawns, flower production, landscaping, erosion control, green manure, improving soil tilth/health, producing pharmaceutical products/drugs, producing food additives, smoking products, pulp production and wood production.

Applicants further teach methods of recognizing variations in the DNA sequence of the Arabidopsis Coil domain of COP1. One method involves the introduction of a nucleic acid molecule (also known as a probe) having a sequence complementary to the Coil domain of the invention under sufficient hybridizing conditions, as would be understood by those in the art. Another method of recognizing DNA sequence variation associated with the Coil domain is direct DNA sequence analysis by multiple methods well known in the art (Ott, 1991). Another embodiment involves the detection of DNA sequence variation in the Coil domain as represented by different plant genera, species, strains, varieties or cultivars. The Coil domain used for the probe can be from any plant for which the Coil domain has been determined. A particularly good probe for dicotyledonous plants would be that coding for the Coil domain of Arabidopsis, while a particularly good probe for a monocotyledonous plant would be that coding for the Coil domain of rice. As discussed previously, the COP1 sequences of both Arabidopsis and rice have been determined and are readily available to one of ordinary skill in the art. In one embodiment, the sequence will bind specifically to one allele of the Coil domain, or a fragment thereof, and in another embodiment will bind to multiple alleles. Such detection methods include the polymerase chain reaction, restriction fragment length polymorphism (RFLP) analysis and single stranded conformational analysis.

Diagnostic probes useful in such assays of the invention include antibodies to the Coil domain of COP1. The antibodies to the Coil domain may be either monoclonal or polyclonal, produced using standard techniques well known in the art (See Harlow & Lane's *Antibodies: A Laboratory Manual*, Cold Spring Harbor Laboratory Press, 1988). They can be used to detect the Coil domain protein by binding to the protein and subsequent detection of the antibody-protein complex by ELISA, Western blot or the like. The Coil domain sequence used to elicit these antibodies can be any of the Coil domain variants discussed above. Antibodies are also produced from peptide sequences of the Coil domain using standard techniques in the art (See *Protocols in Immunology*, John Wiley & Sons, 1994). Fragments of the monoclonals or the polyclonal antisera which contain the immunologically significant portion can also be prepared.

Assays to detect or measure Coil domain polypeptide in a biological sample with an antibody probe may be based on any available format. For instance, in immunoassays where Coil domain polypeptides are the analyte, the test sample, typically a biological sample, is incubated with anti-Coil domain antibodies under conditions that allow the formation of antigen-antibody complexes. Various formats can be employed, such as "sandwich" assay where antibody bound to a solid support is incubated with the test sample; washed, incubated with a second, labeled antibody to the analyte; and the support is washed again. Analyte is detected by determining if the second antibody is bound to the support. In a competitive format, which can be either heterogeneous or homogeneous, a test sample is usually incubated with an antibody and a labeled competing antigen, either sequentially or simultaneously. These and other formats are well known in the art.

The Structural Basis of COP1 Dimerization

Our results show that COP1 acts as a dimer in vivo, and that the COP1 dimer can also be detected in vitro by chemical cross-link analyses (FIG. 1A and 1B). Experiments using the yeast two hybrid assay have further defined the Coil domain of COP1 as necessary and sufficient for mediating COP1 self interaction (FIG. 1C). Evidence for a minor role for the Ring-finger domain in dimerization is also observed in yeast, which is consistent with recent view of Ring-finger as a protein-protein interaction motif (for review see Berg and Shi, 1996; Borden and Freemont; 1996; Saurin et al., 1996). Indeed, involvement of the Ring-finger domain in dimerization was recently implicated. For example, a resolved crystal structure of the dimerization domain of RAG1, a V(D)J recombinant-activating protein, demonstrated an involvement of the Ring-finger domain in dimerization (Bellon et al, 1997).

Figure 3E:
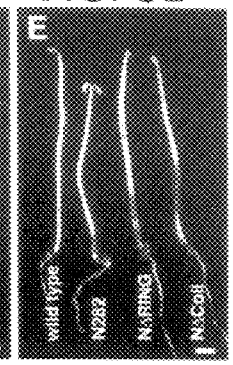
Figure 3F:
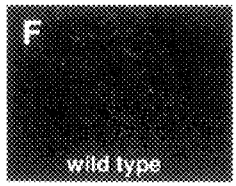
Figure 3G:
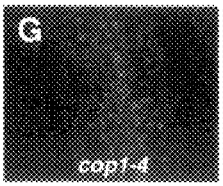
Figure 3H:
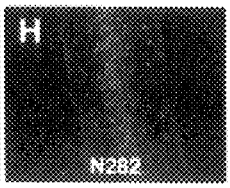
Figure 3I:
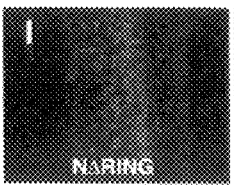
Figure 3J:
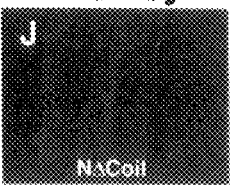

The respective role of the Ring-finger and the Coil domain in COP1 dimerization is consistent with the dominant negative phenotypes of the transgenic seedlings overexpressing COP1 mutant forms that contain these domains. While the N282 fragment (possessing both the Ring-finger and the Coil domains) overexpressors displayed hypersensitive photomorphogenic responses in both dark and light-grown seedlings (FIG. 3E; McNellis et al., 1996), the NΔRING overexpressors did not exhibit seedling de-etiolation in darkness (FIG. 3E). A possible explanation is that the adjacent Ring-finger is required for an effective COP1 self-association in vivo. This would also best explain the severe dominant negative phenotype generated by overexpression of the GUS-COP1-9 mutant protein recently reported (Zhou et al., 1998). In the cop1-9 mutant protein, one and a half WD-40 repeats are missing while intact Ring-finger and the Coil domains are present (McNellis et al., 1994b).

The Structural Basis of Light Regulation of COP1 Nuclear Accumulation

COP1 displays a light-dependent nuclear-cytoplasmic partitioning (von Arnim and Deng, 1994). The reduced nuclear abundance of COP1 under light is presumably a way to prevent COP1 from repressing photomorphogenic development, thus stably maintaining photomorphogenic development commitment. The analysis of GUS fusions with the COP1 domain deletion mutant series revealed that the Ring-finger and the Coil domains may have redundant functions in mediating the light induced depletion of COP1 from the nucleus. Although the mechanism is not known, light could deplete nuclear COP1 abundance by two general means: prevention of import in combination with nuclear COP1 degradation; or active COP1 export. Since there is no precedence for a single protein having two independent domains for mediating nuclear export, it may be more reasonable to speculate that light causes the prevention of nuclear import of COP1. The notion that the Ring-finger domain is a protein-protein interaction motif (for review see Berg and Shi, 1996; Borden and Freemont; 1996; Saurin et al., 1996) would also be consistent with this hypothesis. Recently, specific COP1 interactive proteins were identified that associate with either the Ring-finger domain (K. U. Torii and X. W. Deng, unpublished) or the Coil domain (Matsui et al., 1995; Yamamoto et al., 1998). One such protein, CIP1, has been shown to colocalize with the cytoskeletal structure (Matsui et al., 1995). These interactive proteins could be potential candidates involved in the cytoplasmic retention of COP1. However, our results can not rule out the possibility that the Ring-finger and the Coil domains may each contribute to the structural integrity necessary for the cytoplasmic retention of COP1, while the deletion of both would simply eliminate the conformation or structure necessary for proper cellular localization.

Previous studies revealed that the pleiotropic COP/DET/FUS loci are required for the proper nuclear localization of COP1 in darkness (Chamovitz et al., 1996; von Arnim et al., 1997). Our results indicate that none of the Ring-finger, Coil, or the WD-40 repeats modules are specifically involved in associating with other COP/DET/FUS proteins, as the deletion of any of the domains failed to compromise the nuclear-localization of COP1 in darkness (FIG. 4). It could be that the other COP/DET/FUS proteins act through other regions of COP1, such as NLS or specific individual WD-40 repeat(s). For example, each WD-40 repeat of the yeast TUP1 is capable of interacting with different partners (Komachi et al., 1994). The molecular basis for COP1 interacting with other COP/DET/FUS proteins, both direct and indirect, will be sought out in future work.

The WD40 Repeats Mediate the Repression of Photomorphogenic Development Through an Interaction with HY5, a Positive Regulator of Photomorphogenesis The overexpression of the COP1 mutant forms that retain intact WD-40 repeats caused reduced seedling responses to light (FIGS. 6 and 7). There are at least two possible explanations for this observation. First, the WD-40 repeats region is an autonomous module responsible for mediating repression of photomorphogenesis. Thus the more of this domain is available, the more is the suppression of photomorphogenesis. Second, the intact WD-40 repeats region in the mutated COP1 forms are somehow interfering with an upstream factor(s) to mediating light inactivation of COP1. The fact that the hypocotyl length phenotype conferred by the COP1 domain-deletion overexpressors showed a correlation with the ability of the corresponding COP1 fragments to interact with HY5 in the yeast two-hybrid system (FIGS. 6, 7, and 8) would strictly consistent with the first explanation. Although not mutually exclusive with the second possibility, the observation implies that the WD-40 repeat module of COP1 is required for in vivo repression of HY5 activity through a direct interaction (Ang et al., 1998).

Further, COP1 dimerization is a prerequisite for the functional interaction of the COP1 WD-40 repeat domain and HY5. This is evident since GUS-ΔRΔC overexpressor seedlings display elongated hypocotyl phenotype due to the ability of GUS to confer self-association (FIGS. 6 and 7; Jefferson et al., 1987) and to restore the ability to interact with HY5 (FIG. 8). Taken together, the results indicate that the C-terminal WD-40 repeats are responsible for conferring repression of photomorphogenic seedling development, at least in part by directly interacting with and negatively regulating HY5. It should be noted that all of our experiments were performed in the wild-type background. Our preliminary observations suggest that neither ΔRING nor ΔCoil mutant proteins can rescue the seedling lethality of the cop1 null-allele (C. D. Stoop-Myer and X. -W. Deng, unpublished). This is consistent with the results that both the Ring-finger and the coiled-coil have multiple functions.

The WD-40 repeats have been found in several nuclear proteins that function as transcriptional repressors, such as Drosophila extra sex comb (Esc), yeast Tup1, Hir1, and Met30 (Keleher et al., 1992; Sherwood et al., 1993; Gutjahr et al., 1995; Thomas et al., 1995). These WD-40 proteins do not appear to bind DNA directly, but instead achieve their repressive activities by interacting with sequence-specific DNA-binding transcription factors. Two distinct repression mechanisms have been proposed. One is that the WD-40 proteins repress transcription by interfering with the basal transcriptional machinery, as proposed for Tup1 and Hir1 (Tzamarias and Struhl, 1994; Komachi et al. 1994; Spector et al., 1997). One way to do that is to directly displacing the member of the TFIID complex as proposed for Esc (Gutjahr, et al., 1995). In these cases, the sequence specific DNA-binding proteins may be simply required for recruiting the WD-40 proteins to the target promoters (Tzamaris and Struhl, 1994; Spector et al., 1997). The second mechanism is that the WD-40 proteins sequester sequence-specific transcriptional activators. One such example is yeast Met30 that represses the transcription of sulfur metabolic genes by associating with and inhibiting the bZIP transcriptional activator Met4 (Kuras et al., 1995; Thomas et al., 1995; Kuras et al., 1996). COP1 could act in a mechanism similar to that of Met30 by sequestering HY5 or mask the ability of HY5 to activate transcription.

In conclusion, the work presented here allowed us to assign specific functional roles to the three conserved COP1 domains in the light control of seedling development. It demonstrated that modulating the activity of COP1 domains or modules can alter seedling developmental fate to either more photomorphogenic, such as N282 and the Coil overexpressors, or more skotomorphogenic, such as ΔRING and ΔCoil overexpressors. Therefore, our study provides a structural basis for COP1 functioning as an autonomous molecular switch.

EXAMPLES

Materials and Methods
Induced Mutations

Depending on the context, the term "mutation" variously refers to the process by which a gene undergoes a structural change, a modified gene resulting from such a change or, by extension, an individual manifesting the mutation. Mutation breeding is a process well known to one of ordinary skill in the plant breeding art whereby mutations are induced by mutagens in an effort to develop new crop varieties that can increase agricultural productivity. A mutagen is any physical (e.g., ionizing radiation) or chemical agent (e.g., ethyl methanesulfonate) that raises the frequency of mutation above the spontaneous rate of natural mutations.

For an overview of mutation breeding in plants, see, e.g., Neal F. Jensen, *Plant Breeding Methodology*, Chapter 19, pp. 249–255, John Wiley & Sons (1988); N. W. Simmonds, *Principles of Crop Improvement*, pp. 297–314, Longman (1979); and R. W. Allard, Principles of Plant Breeding, Chapter 35, pp. 444–454, John Wiley & Sons (1960).

Value of Plant Transformation

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as resistance to an insect pest, and to introduce these genes into already useful varieties of plants. Once the foreign genes have been introduced into a plant, that plant can than be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome.

Homologous recombination and site-directed integration in plants are discussed in U.S. Pat. Nos. 5,451,513, 5,501, 967 and 5,527,695.

Transformation Methods

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and Agrobacterium-mediated transformation (see, e.g., U.S. Pat. Nos. 5,405,765, 5,472,869, 5,538,877, 5,538,880, 5,550,318, 5,641,664, 5,736,369 and 5,736369; Watson et al., *Recombinant DNA*, Scientific American Books (1992); Hinchee et al., *Bio/Tech.* 6:915–922 (1988); McCabe et al., *Bio/Tech.* 6:923–926 (1988); Toriyama et al., *Bio/Tech.* 6:1072–1074 (1988); Fromm et al., *Bio/Tech.* 8:833–839 (1990); Mullins et al., *Bio/Tech.* 8:833–839 (1990); and, Raineri et al., *Bio/Tech.* 8:33–38 (1990)).

Transgenes

Genes successfully introduced into plants using recombinant DNA methodologies include, but are not limited to, those coding for the following traits: seed storage proteins, including modified 7S legume seed storage proteins (U.S. Pat. Nos. 5,508,468, 5,559,223 and 5,576,203); herbicide tolerance or resistance (U.S. Pat. Nos. 5,498,544 and 5,554, 798; Powell et al, *Science* 232:738–743 (1986); Kaniewski et al., *Bio/Tech.* 8:750–754 (1990); Day et al., *Proc. Natl. Acad. Sci. USA* 88:6721–6725 (1991)); phytase (U.S. Pat. No. 5,593,963); resistance to bacterial, fungal, nematode and insect pests, including resistance to the lepidoptera insects conferred by the Bt gene (U.S. Pat. Nos. 5,597,945 and 5,597,946; Hilder et al, Nature 330:160–163; Johnson et al., *Proc. Natl. Acad. Sci. USA*, 86:9871–9875 (1989); Perlak et al., *Bio/Tech.* 8:939–943 (1990)); lectins (U.S. Pat. No. 5,276,269); and flower color (Meyer et al., *Nature* 330:677–678 (1987); Napoli et al., *Plant Cell* 2:279–289 (1990); van der Krol et al., *Plant Cell* 2:291–299 (1990)).

Expression Units to Express Exogenous DNA in a Plant

As provided above, several embodiments of the present invention employ expression units (or expression vectors or systems) to express an exogenously supplied nucleic acid sequence, such as the sequence coding for N282 protein in a plant. Methods for generating to expression units/systems/vectors for use in plants are well known in the art and can readily be adapted for use in expressing the N282 protein in a plant cell. A skilled artisan can readily use any appropriate plant/vector/expression system in the present methods following the outline provided herein.

The expression control elements used to regulate the expression of the protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumafacians*. Alternatively, plant viral promoters can also be used, such as the cauliflower mosaic virus 35S promoter to control gene expression in a plant. Lastly, plant promoters such as prolifera promoter, fruit-specific promoters, Ap3 promoter, heat shock promoters, seed-specific promoters, etc. can also be used. The most preferred promoters will be most active in seedlings.

Either a constitutive promoter (such as the CaMV or Nos promoter), an organ-specific promoter (such as the E8 promoter from tomato) or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a preexisting vector. In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the Agrobacterium octopine synthase signal (Gielen et al., *EMBO* 3: 835–846 (1984)) or the nopaline synthase signal (Depicker et al., *Mol. and Appl. Genet.* 1: 561–573 (1982)).

The resulting expression unit is ligated into or otherwise constructed to be included in a vector which is appropriate for higher plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

The Coil domain sequences of the present invention can also be fused to various other nucleic acid molecules such as Expressed Sequence Tags (ESTs), epitopes or fluorescent protein markers.

ESTs are gene fragments, typically 300 to 400 nucleotides in length, sequenced from the 3' or 5' end of complementary-DNA (cDNA) clones. Nearly 30,000 *Arabidopsis thaliana* ESTs have been produced by a French and an American consortium (Delseny et al., *FEBS Lett.* 405(2):129–132 (1997); Arabidopsis thaliana Database, http://genome.www.stanford.edu/Arabidopsis). For a discussion of the analysis of gene-expression patterns derived from large EST databases, see, e.g., M. R. Fannon, *TIBTECH* 14:294–298 (1996).

Biologically compatible fluorescent protein probes, particularly the self-assembling green fluorescent protein (GFP) from the jellyfish *Aequorea Victoria*, have revolutionized research in cell, molecular and developmental biology because they allow visualization of biochemical events in living cells (Murphy et al., *Curr. Biol.* 7(11):870–876 (1997); Grebenok et al., *Plant J.* 11(3):573–586 (1997); Pang et al., *Plant Physiol.* 112(3) (1996); Chiu et al., *Curr. Biol.* 6(3):325–330 (1996); Plautz et al., *Gene* 173(1):83–87 (1996); Sheen et al., *Plant J.* 8(5):777–784 (1995)).

Site-directed mutatgenesis has been used to develop a more soluble version of the codon-modified GFP call soluble-modified GFP (smGFP). When introduced into Arabidopsis, greater fluorescence was observed when compared to the codon-modified GFP, implying that smGFP is 'brighter' because more of it is present in a soluble and functional form (Davis et al, *Plant Mol. Biol.* 36(4):521–528 (1998)). By fusing genes encoding GFP and beta-glucuronidase (GUS), researchers were able to create a set of bifunctional reporter constructs which are optimized for use in transient and stable expression systems in plants, including Arabidopsis (Quaedvlieg et al., *Plant Mol. Biol.* 37(4):715–727 (1998)).

Berger et al. (*Dev. Biol.* 194(2):226–234 (1998)) report the isolation of a GFP marker line for Arabidopsis hypocotyl epidermal cells. GFP-fusion proteins have been used to localize and characterize a number of Arabidopsis genes, including geranylgeranyl pyrophosphate (GGPP) (Zhu et al., *Plant Mol. Biol.* 35(3):331–341 (1997).
Disabling Genes An example of an effective disabling modification would be a single nucleotide deletion occurring at the beginning of a gene that would produce a translational reading frameshift. Such a frameshift would disable the gene, resulting in non-expressible gene product and thereby disrupting functional protein production by that gene. Protease production by the gene could be disrupted if the regulatory regions or the coding regions of the protease genes are disrupted.

In addition to disabling genes by deleting nucleotides, causing a transitional reading frameshift, disabling. modifications would also be possible by other techniques including insertions, substitutions, inversions or transversions of nucleotides within the gene's DNA that would effectively prevent the formation of the protein coded for by the DNA.

It is also within the capabilities of one skilled in the art to disable genes by the use of less specific methods. Examples of less specific methods would be the use of chemical mutagens such as hydroxyl amine or nitrosoguanidine or the use of radiation mutagens such as gamma radiation or ultraviolet radiation to randomly mutate genes, such as the COP1 gene. Such mutated strains could, by chance, contain disabled COP1 genes such that the genes were no longer capable of producing functional proteins for any one or more of the domains. The presence of the desired disabled genes could be detected by routine screening techniques. For further guidance, see U.S. Pat. No. 5,759,538.
Antisense Encoding Vectors Methods for inhibiting expression in plants using antisense constructs, including generation of antisense sequences in situ are described, for example, in U.S. Pat. Nos. 5,107,065 and 5,254,800.

Other methods that can be used to inhibit expression of an endogenous gene in a plant may also be used in the present methods. For example, formation of a triple helix at an essential region of a duplex gene serves this purpose. The triplex code, permitting design of the proper single stranded participant is also known in the art. (See H. E. Moser, et al., *Science* 238: 645–650 (1987) and M. Cooney, et al., *Science* 241: 456–459 (1988)). Regions in the control sequences containing stretches of purine bases are particularly attractive targets. Triple helix formation along with photocrosslinking is described, e.g., in D. Praseuth, et al., *Proc. Nat'l Acad. Sci. USA* 85: 1,349–1,353 (1988).
Breeding Methods 1. Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population which is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

2. Mass Selection. In mass selection, desirable individual plants are chosen, harvested, and the seed composited without progeny testing to produce the following generation. Since selection is based on the maternal parent only, and their is no control over pollination, mass selection amounts to a form of random mating with selection. As stated above, the purpose of mass selection is to increase the proportion of superior genotypes in the population.

3. Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100–200 being the average. Broad based synthetics formed from 100 or more clones would be expected to be more stable during seed multiplication than narrow based synthetics.

4. Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an outbreeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity which results in increased vigor of growth, survival, and fertility of hybrids as compared with the parental lines which were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed to Production* 8:161–176, *In Hybridization of Corp Plants*, supra. Plant Materials and Growth Conditions Plant growth conditions were exactly as described by McNellis et al. (1994a) unless otherwise described in the text. Full-length COP1, N282, and ΔRING overexpressors are in the No-O ecotype, and all other transgenic plants are Columbia ecotype. Wild-type seedlings of both ecotypes were used as controls, while only one (Columbia unless stated otherwise) was shown in most Figures.

While not wanting to be bound by specific definitions of different light intensities, low light generally refers to a light intensity of around 50 to 200 $mE/m^{-1}/sec^2$; high light generally refers to a light intensity of above 400 or 450 $mE/m^{-1}/sec^2$; and extremely low light generally refers to a light intenstity of <1 $mE/m^{-1}/sec^2$. To optimize phenotype examination, light intensities were changed in some experiments as described in the text.

Construction of COP1 Domain Cassettes

To facilitate the further cloning procedures, all of the COP1 domain deletion constructs were first cloned into the modified pBluescript KS vector (pKSm; Deng et al., 1992). pKS-ΔRING was constructed by replacing the BamHI-XbaI fragment of pKS-COP1 with that of pMALΔZn (von Arnim and Deng, 1993). pKS-ΔRING was cleaved with BamHI and MscI, and inserted into pKS-N282 (McNellis et al., 1996) to generate pKS-NΔRING. To construct pKS-NΔCoil, two sets of primers, T7 and CCNT3 (5' CCG CTC GAG CCG AAA CTG ATC CAA GGG CGA 3') (SEQ ID NO:5), and CCCT5 (5' CCG CTC GAG AAG TTG CGG ATG CTC GGA GA 3') (SEQ ID NO:6) and T3, were used to amplify the coding regions N-terminal (amino acid 1 to 127) and C-terminal (amino acid 216 to 282) of Coil domain, respectively. Both fragments were cloned into the pKSm vector to generate pKS-ΔC.nt and pKS-ΔC.ct, respectively. pKS-ΔC.nt insert was cleaved by XhoI, and inserted into the XhoI-digested pKSΔC.ct to generate pKS-NΔCoil. To generate pKS-NΔΔ, the PCR was performed using NΔRING as a template with a primer combination T7 and NT-Sal3 (5' A CGC GTC GAC CCC AAA CTG ATC CAA GGG CGA 3') (SEQ ID NO:7). The amplified fragment was cloned into the pKSm vector to generate pKS-ΔΔ.nt. pKS-ΔΔ.nt was cut with SalI, and the released fragment was inserted into the XhoI-cleaved pKSΔC.ct to generate pKS-NΔΔ. The BamHI-MscI fragments of pKS-NΔCoil and pKS-NΔΔ were replaced with that of pKS-COP1 to generate pKS-ΔCoil and pKS-ΔΔ, respectively. To generate pKS-Coil and pKS-RING, the PCR was performed using pKS-N282 as a template with primer combinations Coil5 (5° CAT GCC ATG GAT AAG CTA TTG AAG AAA ACT 3') (SEQ ID NO:8) and Coil3 (5' CCG CTC GAG TTA GTC CCT AGC TCG GTA TAA ATC 3') (SEQ ID NO:9), or RING5 (5' CAT GCC ATG GTT GGT GAA GGT GCT AAT CGT 3') (SEQ ID NO:10) and RING3 (5' CCG CTC GAG TTA TGA CAC ATG CCG AGC TGA AGT 3') (SEQ ID NO:11), respectively. The amplified fragments were digested with NcoI and XhoI, and inserted into pKSm. For pKS-Coil and pKS-RING, leucine at aa104 and serine at aa21, respectively, were replaced with methionine. The sequences of all clones constructed using the PCR methods have been confirmed by sequencing the resulting clones. pKS-cop1-10 was generated by replacing the XbaI and XhoI-digested fragment with that of pTA-fus1-4 (McNellis et al., 1994a). The BamHI-XbaI fragment of pKS-cop1-10 was then replaced with that of pKS-ΔRING to generate pKS-ΔRΔG4, which lacks the Ring-finger and the last repeat of the WD-40.

Construction of Expression Cassettes and Stable Transformation of Arabidopsis

For 35S-ΔRING expression cassette, pMALΔZn was digested with EagI and HindIII, blunt ended with Klenow enzyme, and used to replace the GUS gene in pRTL2-GUS (Restrepo et al. 1990). The GUS gene was excised from pRTL2-GUS by cutting the plasmid with NcoI and BamHI, and blunt-ended with Klenow. 35S-ΔRING expression constructs were ligated as HindIII fragments into the binary plant transformation vector pBIN19. Arabidopsis plants of the No-O ecotype were transformed using the tissue culture procedure as described in McNellis et al. (1994b).

For 35S-ΔCoil, 35S-ΔRΔC, and 35S-ΔRΔG4, the corresponding pKSm cassettes were cleaved with NcoI and BglII, and ligated into the NcoI and BamHI-digested pRTL2-GUS. For 35S-NΔRING and 35S-NΔCoil, the corresponding pKSm cassettes were digested with NcoI and EcoRV, and ligated into the pRTL2-GUS vector which has been cut with BamHI, blunt-ended, and recut with NcoI. For 35S-GUS_ΔRING, 35S-GUS_ΔCoil, 35S-GUS_ΔΔ35S-GUS_ΔRΔG4, the corresponding pKSm cassettes were cleaved with BglII, and ligated into the BglII and BamHI-cleaved pRTL2-GUSNIaΔBam. These pRTL cassettes were then cleaved with either HindIII or PstI and ligated into pPZP222 (Hajdakiewics et al., 1994). The resulting clones were then electroporated into Agrobacterium strain GV3101 (pMP90). Arabidopsis plants of ecotype Columbia were transformed by the vacuum infiltration method (Bechtold et al., 1993). ΔRING transgenic seedlings were selected with Kanamycin (40 μg/ml; Sigma) and transgenic seedlings for the rest of all constructs were selected with Gentamycin (100 μg/ml; Sigma).

Five, five, seven, nine, seven, and five independent transgenic lines for 35S::NΔRING, 35S::ΔRING, 35S::NΔCoil, 35S::ΔCoil, 35S::ΔRΔC, and 35S::ΔRΔG4, respectively, were confirmed for a single T-DNA insertion and accumulation of the transgene products (data not shown). For COP1 localization analysis, four, five, three, and three independent lines for GUS-ΔRING, GUS-ΔCoil, GUS-ΔRΔC, and GUS-ΔRΔG4, respectively, were confirmed for a single T-DNA insertion, GUS activity, and for the accumulation of the transgene products (data not shown). For those transgenic lines with phenotypes, the co-segregation of the phenotype and the transgenes were established by a previous procedure (McNellis et al., 1996). Either T3 seedlings homozygous for the transgene or T2 seedlings displaying antibiotic resistance were used for analysis. T2 seeds of one GUS-ΔCoil (line 8) and three GUS-ΔRΔC lines segregated one-quarter of fusca phenotype seedlings (data not shown). They displayed extreme accumulation of anthocyanins, as do COP1 strong or lethal alleles, and often failed to survive (data not shown). All fusca seedlings were gentamycin resistant and had extremely reduced level of the GUS activity and the transgene accumulation (data not shown). Thus, cosuppression events were suspected for these fusca seedlings. A consistent 1:2:1 segregation at T2 and T3 generations for to gentamycin sensitive (wild-type): gentamycin resistant (overexpressor): gentamycin resistant (cosuppressor) suggests a dosage dependent mechanism for cosuppression (data not shown). However, this phenomenon was not studied further, since it was not the primary object of our research. For GUS-ΔRΔC lines, overexpressors that comprise one-half of the T2 population were used for further analysis.

Yeast Two-hybrid Analysis pKS-RING and pKS-Coil are digested with EcoRI and XhoI, and rest of the COP1 domain cassettes in the pKSm vectors were digested with EcoRI. Fragments were then ligated into pEG202 or pJG4–5 to generate COP1 domains fused to the LexA DNA binding protein or the synthetic activation domain, respectively (Golemis et al., 1995). Generation of pEG-N282, pJG-N282, pJG-COP1, and pJG-ΔRING was described elsewhere (McNellis et al., 1996; Ang et al., 1998). To generate pJG-GUS-ΔRΔC, pRTL-GUS-ΔRΔC was cleaved with NcoI and XbaI and then ligated into NcoI/XbaI digested pKS-COP1; The resulted plasmid was cleaved with EcoRI and inserted into pJG4–5. Transformation of yeast strain EGY48-0 (Golemis et al., 1995) with bait, prey, and reporter plasmids (pSH18–34), and subsequent β-galactosidase activity assay was performed as described in McNellis et al.(1996). For unknown reasons, we could not stably express LexA-COP1 protein, either under ADH or inducible GAL1 promoters (data not shown); therefore, we could not test the full-length COP1-COP1 interaction in yeast.

GUS Cytochemical Staining and Confocal Laser Scanning Microscopy

GUS cytochemical staining of Arabidopsis transformants was performed as described in von Arnim and Deng (1994). For the Confocal Laser Scanning Microscopy, freshly grown seedlings in GM plates under continuous white light were harvested and directly observed using a Biorad 1024 cofocal microscope with the Rhodomin filter.

Protein Gel Blot, in vitro Translation, Chemical Cross-Linking, and Gel Filtration Chromatography Protein immunoblot analysis was performed exactly as described previously (McNellis et al., 1994a). pAR-COP1, a FLAG-tagged COP1 that has an additional peptide DDADT-KDDDDK at the N-terminus (Matsui et al., 1995), was in vitro transcribed and translated using TNT coupled reticulocyte lysate system (Promega) and radiolabelled with [$^{35}$S] methionine (Amersham). For chemical cross-linking, 2 μl of translation mix (with radiolabelled proteins) was diluted to 18 μl with a reaction buffer (100 mM potassium phosphate [pH 7.7]; 100 mM NaCl; 0.1 mM ZnSO$_4$; 10% glycerol; 0.1% NonidetP-40; 4 mM DTT) and cross-linked with 2 μl of freshly diluted Dsub or EGS in dimethyl sulfoxide. For a negative control, 2 μl of dimethyl sulfoxode was added to the reaction. After 20 min incubation at room temperature, the reaction was quenched by addition of 2 μl of 1 M glycine (for Dsub) or 200 mM lysine (for EGS) and 22 μl of 2×Laemmli SDS-PAGE buffer. Samples were boiled for 5 min, separated by 6% SDS-PAGE, and fluorographed after treatment with Amplify (Amersham).

For gel filtration chromatography, 8-day-old light- or dark grown seedlings were homogenized with 2×gel filtration buffer containing 50 mM Tris-HCl (pH 7.5), 440 mM NaCl, 2 mM MgCl$_2$, 2 μM ZnSO$_4$, 0.5 mM PMSF and centrifuged for 5 min at 4° C. Total soluble protein was fractionated through a 25 ml Superdex-200 FPLC column (Pharmacia)

with 1×gel filtration buffer at a flow rate of 0.5 ml/min. All procedures were carried out at 4° C. and, for dark samples, under dim green safe light. Consecutive fractions of 0.5 ml each were collected after the void volume (7.5 ml), concentrated, and subjected to 10% SDS-PAGE followed by a protein immunoblot analysis. The molecular weight standards for size estimation of the native COP1 protein were as follows: blue dextran (void); thyroglobulin (669 kDa); ferritin (440 kDa); catalase (232 kDa); aldolase (158 kDa); BSA (67 kDa); ovalbumin (43 kDa); and ribonuclease A (13.7 kDa) (Sigma).

Example 1

COP1 Forms a Dimer in vitro and in vivo

We have reported that the N282 fragment of COP1, which contains both the Ring-finger and Coil regions, possesses the ability to interact with the full-length COP1 in a yeast two-hybrid system, implying that COP1 may function as a homodimer or multimer (McNellis et al., 1996). To better understand the COP1 self-association, we performed a chemical cross-linking analysis of in-vitro translated COP1 protein in solution. A FLAG-COP1 epitope tagged protein was in-vitro translated and then cross-linked with either dimethylsuberimidate (DSub) or ethylene glycobis (succinimidylsuccinate) (EGS). FIG. 1A shows monomeric FLAG-COP1 (78 kDa) and the cross-linked products resolved by SDS-PAGE and detected by fluorography. Cross linking with either Dsub or EGS generated a band with apparent molecular size of approximately 160 kDa, clearly indicating dimer formation in vitro (FIG. 1A).

To confirm the presence of COP1 dimers in vivo, a gel-filtration analysis was performed using protein extracts from light- or dark-grown Arabidopsis wild-type seedlings. As shown in FIG. 1B, the endogenous Arabidopsis COP1 protein fraction peaked at approximately 160 kDa region, very close to the size of the cross-linked dimer in vitro. However, the COP1 peak was very broad and contained a broad shoulder toward the larger molecular size fractions (FIG. 1B). Therefore it is possible that a portion of COP1 may present as homo-oligomers or in heterogeneous associations with other molecules in vivo. Further, the limited resolution of the gel-filtration can not rule out the presence of a minor amount of COP1 as monomer since the shoulder of the COP1 peak at the smaller molecular weight side extended toward the 70 kDa region. Although the relative amount and distribution of the COP1 doublet bands (due to partial degradation in the extracts) is somewhat variable from experiment to experiment, the gel-filtration profiles of both the light- and dark-grown seedlings were essentially identical (FIG. 1B), indicating that light does not affect COP1 self-association in vivo.

Example 2

COP1 Dimerizes Through the Coil Domain

To further delimit the COP1 dimerization domain within N282 fragment of COP1, a series of deletion mutants of N282 were constructed and analyzed using the yeast two-hybrid assay (FIG. 1C). The result indicates that the Coil domain of COP1 was shown to be both necessary and sufficient for self association (FIGS. 1C3, 1C4, 1C7 to 12C10). However, the deletion of the Coil from the N282 fragment still retained some weak and reproducible interactions slightly higher than negative controls (see FIGS. 1C1 to 1C4), suggesting the presence of residual COP1 self-association within the rest of the N-terminal region. The Ring-finger domain seems responsible for this residual activity since this domain showed weak interaction with itself (FIG. 1C5). A supportive role for the Ring-finger in COP1 intramolecular association became evident among the constructs with intact C-terminus (FIGS. 1C11 to 1C14): deletion of the Coil domain still retained a weak interaction (FIG. 1C13), while the deletion of both the Ring-finger and the Coil domains completely abolished the interaction (FIG. 1C14). The disruption of the WD-40 repeats also perturbed the intramolecular interaction (FIG. 1C15), possibly due to a conformational hindrance caused by misfolded WD-40 repeats domain. Protein gel immunoblot analysis did not reveal any significant differences in expression levels of those domain-deletion constructs (data not shown). Thus, it rules out the possibility that the different activities in the yeast two hybrid interaction assay were caused by different expression levels of the proteins.

Example 3

Overexpression of the Coil Region Confers Seedling Hyperphotomorphogenic Development If the Coil domain has a major role for COP1 dimerization, it may represent the domain primarily responsible for the observed dominant negative phenotype in N282 overexpression plants (McNellis et al., 1996). To test this, transgenic Arabidopsis plants expressing two N-terminal COP1 mutant forms under the strong CaMV35S promoter were generated. As shown in FIG. 2A, NΔRING and NΔCoil are essentially the N282 fragment of COP1 lacking the Ring-finger or the Coil domain, respectively. Protein gel immunoblot analysis with anti-COP1 antibody of three representative NΔRING and NΔCoil transgenic lines suggested that all lines accumulated transgene products at comparable or higher level than that of the N282 overexpressors (FIG. 2B, McNellis et al., 1996). In all transgenic lines examined, the level of the endogenous COP1 protein appeared to be unaltered (FIG. 2B).

Transgenic Arabidopsis seedlings were examined under different light conditions and in darkness (FIG. 3). The overexpression of NΔRING conferred a dramatic reduction in hypocotyl length when seedlings were grown under continuous white, far-red, red, and blue light (FIGS. 3A to 3D). In addition, NΔRING seedlings displayed an excessive accumulation of anthocyanin in the upper hypocotyls (see FIG. 3B). Furthermore, the overexpression of NΔRING as well as N282 led to ectopic chloroplast differentiation in seedling roots (FIGS. 3F to 3J). Hence, the overexpression of the NΔRING is sufficient to impair the endogenous COP1 function and to enhance the light signaling mediated by multiple photoreceptors. In contrast to the NΔRING overexpressors, NΔCoil overexpressors did not confer any visible phenotypes, indicating that the Ring-finger domain itself is insufficient for causing any dominant-negative effects (FIG. 3 A–E, and J). Although some NΔCoil overexpressors (lines 2 and 3, FIG. 2B) contain partial degradated forms (FIG. 2B), they could not be the cause for the lacking of the phenotype in those NΔCoil overexpressors since other lines (such as line 1) do not contain the same partial degradation products and also exhibit no phenotype.

The NΔRING overexpressors did not show any de-etiolation phenotype in darkness (FIG. 3E). Since the overexpression of N282 conferred a partial de-etiolation in darkness (McNellis et al., 1996), it seems to indicate that an effective functional interference with the endogenous COP1 in darkness requires the additional Ring-finger domain. A supportive role for the Ring-finger in COP1 dimerization (FIG. 1C) is consistent with this observation.

Example 4

The Ring-finger and the Coil Domains Act Redundantly to Mediate Light Induced Depletion of COP1 from Nucleus Light signals negatively regulate COP1 abundance in the nucleus (von Arnim and Deng, 1994; von Arnim et al., 1997). In darkness, GUS-COP1, a full-length COP1 fused to a reporter β-glucuronidase, predominantly localizes in the nucleus, but the transfer of seedlings from dark to light reduces nuclear abundance of GUS-COP1 (von Arnim and Deng, 1994). To identify the domain(s) that mediates the light responsiveness of COP1, the subcellular localization of the fusion proteins of GUS fusions with COP1 deletion mutants were examined. For this purpose, the GUS protein was fused to the N-terminus of the COP1 fragments that lack either the Ring-finger (GUS-ΔRING), or the Coil (GUS-ΔCoil), or both Ring-finger and Coil (GUS-ΔRAΔC), or the Ring-finger and the last repeat of the WD-40 motif (GUS-ΔRΔG4). Transgenic Arabidopsis plants that express the four constructs under the CaMV35S promoter were produced and examined.

FIG. 4 shows representative GUS staining patterns in hypocotyl cells of dark- or light grown transgenic Arabidopsis. In darkness, all GUS-fusion constructs localized in the nucleus and similar to that described for GUS-COP1 (von Arnim and Deng, 1994), suggesting that the NLS remains functional in all the mutated forms of COP1. This result is consistent with a site-directed mutagenesis study that revealed the COP1 NLS is contained within amino acids 293–314 (A. G. von Arnim, personal communication). When seedlings were grown under high intensity continuous white light (150 μmole m$^{-2}$ sec$^{-1}$), GUS-ΔRING, GUS-ΔCoil, and GUS-ΔRΔG4 chimeric proteins were excluded from the nucleus (FIGS. 4A, 4B, and 4D). In contrast, GUS-ΔRΔC displayed a constitutive nuclear localization in hypocotyl cells (FIG. 4C), as well as in cotyledon epidermis- and mesophyll cells of light-grown seedlings (data not shown). The data suggests that while the deletion of the RING finger or the Coil alone does not significantly affect the light activated nuclear depletion of COP1, deletion of both domains clearly compromises light regulation of COP1 nuleocytoplasmic partitioning.

Example 5

C-terminal WD-40 Repeat Domain has Essential but not Self-sufficient Role in Repressing Light Inhibition of Hypocotyl Elongation To reveal the function of the WD-40 repeats, we first generated transgenic Arabidopsis plants overexpressing only the COP1 C-terminal region (amino acid 283–675) which contains the entire WD-40 repeats. All transgenic lines with this construct failed to accumulate any detectable amount of the mutated COP1 (data not shown). Therefore, we generated a new set of COP1 domain deletion constructs which specifically lack the Ring-finger (ΔRING) or the Coil (ΔCoil) or both (ΔRΔC) in the full-length COP1 context and are driven by the CaMV 35S to promoter (FIG. 5A). As a negative control, a construct that lacks the last repeat of the WD-40 motif in addition to the RING finger deletion (ΔRΔG4) was also generated. The Ring-finger was not included in this control construct since its deletion does not influence the effect mediated by WD-40 repeats (see later). As shown in FIG. 5B, protein gel immunoblot analysis of ΔRING, ΔCoil, ΔRΔC, and ΔRΔG4 overexpressors indicated that all COP1 mutant forms accumulate to similar levels and their expression does not affect the level of endogenous COP1. Therefore, the severity of the phenotypes is most likely due to the effectiveness of the mutated forms of COP1.

Seedling phenotypes of the ΔRING, ΔCoil, ΔRΔC, and ΔRΔG4 overexpressors were examined under continuous white, blue, and far-red light conditions. As shown in FIGS. 6 and 7, ΔRING seedlings displayed long hypocotyl phenotypes in all light conditions tested, similar to that of the full-length COP1 overexpressor (McNellis et al., 1994b). ΔCoil seedlings displayed a subtle but statistically significant hy phenotype only under blue light (FIGS. 6B and 7B). This weak but reproducible phenotype in the ΔCoil line is consistent with the fact that deletion of the Coil domain still retains a weak self association in the yeast (FIGS. 1C11 to 1C14). Thus, the Ring-finger seems dispensable, while the Coil is important but not essential, for repressing seedling photomorphogenic development in our transgenic assay. The effect of ΔRING overexpression was completely abolished by an additional disruption of WD-40 repeats (ΔRΔG4), indicating a critical role for the intact WD-40 repeat domain in repressing photomorphogenic development. ΔRΔC did not confer any detectable phenotypes under any light conditions tested (FIGS. 6 and 7). Thus, the C-terminal WD-40 domain alone is not self-sufficient for conferring the repressive activity of photomorphogenesis.

Example 6

The ΔCoil Defect can be Largely Compensated by the Addition of a Heterologous Self Association Protein Motif Since the Coil domain mediates COP1 self association, the involvement of the Coil domain in repressing seedling photomorphogenesis may simply due to this structural role. If this is the case, the addition of a new self-association domain to the COP1 ΔCoil mutants may compensate the defects caused by the Coil domain deletion. To test this hypothesis, we examined phenotypic effects of the GUS fusion series with COP1 and its mutated forms since the GUS protein is capable of self-tetramerization (Jefferson et al., 1987). As shown previously, GUS-COP1 overexpression confers a long hypocotyl phenotype similar to the full-length COP1 overexpressors (von Arnim and Deng, 1994; von Arnim et al., 1997). While GUS-ΔRING and ΔRING overexpressors conferred a similar degree of long hypocotyl phenotype, GUS-ΔCoil and GUS-ΔRΔC overexpressors exhibit enhanced seedling long hypocotyl phenotypes when compared to the ΔCoil and ΔRΔC overexpressors (FIGS. 6 and 7). Protein gel blot analysis did not reveal significant differences in the accumulation of transgene products among GUS-ΔCoil, GUS-ΔRΔC, ΔCoil, and ΔRΔC transgenic lines (data not shown). Therefore, our results suggests that fusing a GUS protein can somehow restore the defects of ΔCoil and ΔRΔC in repressing photomorphogenesis, probably by providing a new self association function replacing that of the Coil motif. In contrast, GUS-ΔRΔG4 overexpressors failed to restore long hypocotyl phenotypes (FIGS. 6 and 7), suggesting that the function of the WD-40 repeats cannot be compensated for by the GUS fusion. Therefore, we propose that the WD-40 repeat domain plays a direct role in mediating the repression of photomorphogenesis, while the Coil domain provides the dimerization function of COP1 that is a prerequisite for the proper function of the WD-40 repeats.

Example 7

The WD-40 Repeat Domain Mediates the Functional Interaction Between COP1 and HY5, a Positive Regulator of Photomorphogenesis COP1 represses photomorphogenic development by directly interacting and negatively regulating specific transcription factors that are responsible for promoting photomorphogenic development (Ang et al., 1998; Yamamoto et al., 1998). Since HY5 plays a role in the light regulation of hypocotyl elongation, we examined whether the repressive effect of COP1 is mediated through HY5 and whether the WD-40 repeat domain of COP1 is responsible for the regulatory protein-protein interaction. As shown in FIG. 8, the strength of the interaction of HY5 and a series of COP1 domain deletion mutants in the yeast two hybrid assay is directly correlated to the hypocotyl length conferred by the overexpression of the corresponding COP1. mutant forms (FIGS. 6 and 7). For example, HY5 showed a similar degree of interaction with full-length COP1and ΔRING, reduced interaction with ΔCoil, and no interaction with ΔRΔC__and ΔRΔG4 (FIG. 8).

To examine the specific roles of the WD-40 repeats and the Coil domains in mediating the COP1 and HY5 interaction, we further analyzed HY5 interactions with the GUS-ΔRΔC mutant. Similar to the observed phenotypic effects of GUS-ΔRΔC and ΔRΔC in transgenic seedlings (FIGS. 6 and 7), the GUS-ΔRΔC fusion protein restored the ability of the COP1 mutant form to interact with HY5 (FIG. 8). The result further substantiated the notion that the C-terminal WD-40 repeats of COP1 play a direct role in mediating interaction with HY5 while the dimerization of COP1, which is mediated by the Coil domain, is required for this interaction.

Example 8

Comparison of Seedling Characteristic for Wildtype and Transformed Plants

Using the procedures set forth above, wildtype Arabidopsis plants were transformed with nucleotides coding for the entire N282 fragment of the COP1 gene, including both the Ring-finger and Coil domains, or with nucleotides coding for amino acids at positions 1–38 and 104–282 of the COP1 gene (i.e., the N282 sequence minus the nucleotides coding for the Ring-finger domain). Wildtype plants and plants of the two transformed genotypes were tested in high light, low light and darkness for the relative degree of stem elongation and the relative amount of leaf expansion. The results are provided in the following table:

| Morphological Response | Light Level | Wildtype plants with intact COP1 gene | Wildtype plants transformed with N282, including the Ring-finger + Coil domains | Wildtype plants transformed with N282 minus the Ring-finger domain (NΔRING) |
|---|---|---|---|---|
| Stem Elongation | High Light | Short | Short | Short |
| | Low Light | Long | Short | Short |
| | Darkness | Very Long | Very Long | Very Long |
| Leaf | High Light | Yes | Yes | Yes |
| Expansion | Low Light | Yes | Yes | Yes |
| | Darkness | No | Yes | No |

As shown above, all three plant types displayed wildtype stem elongation when grown under both high light conditions and in darkness. However, it was unexpectedly discovered that both types of transformed plants (N282 and NΔRING) demonstrated shorter stem growth than wildtype plants when grown under low light conditions. All three plant types showed wildtype leaf expansion when grown under both high and low light conditions. However, it was unexpectedly discovered that while the N282-transformed plants displayed unnatural leaf expansion when grown in the darkness, the wildtype and NΔRING-transformed displayed no leaf expansion under the same conditions.

These results demonstrate that wildtype plants transformed with an N282 sequence minus the Ring-finger domain (NΔRING) unexpectedly display: 1) a degree of stem elongation under low light which is similar to the N282-transformed plants and 2) a degree of leaf expansion under extremely low light or darkness which is similar to that of wildtype plants. Thus, the NΔRing-transformed plants (i.e., a transformed plant which comprises a native COP1 gene and, separately, a nucleotide sequence coding for the Coil domain of the COP1 gene, wherein the plants do not have separate expressible nucleotide sequences coding for either the Ring-finger domain of the COP1 gene or for the WD-40 domain of the COP1 gene associated with said Coil domain nucleotide sequence) unexpectedly combined the highly desirable characteristics of reduced leaf expansion under extremely low light or darkness with short hypocotyls under low light.

As discussed previously in the Background section, it is agronomically and horticulturally desirable to have seedlings which combine a lack of leaf expansion under complete darkness, such as during pre-emergence growth phases, with shorted stem elongation under low light levels after emergence. Here, the plants transformed with a nucleotide sequence which encodes the Coil domain, and not an expressible Ring-finger domain, are the only plants to combine these desirable characteristics.

Example 9

Production of Stably Transformed Transgenic Tomato Lines Using the Coil Domain Sequence As discussed above, Frances et al. (1998) have established that tomato plants inherently contain a homologue of the Arabidopsis COP1 gene, designated TCOP1.

The Arabidopsis Coil domain expression construct is ligated as HindIII fragments into the binary plant transformation vector pBIN19 as set forth in the Materials and Methods. Tomato plants (*Lycopersicon esculentum*, var. Better Boy) are transformed with the resultant vector according to published procedures (see, e.g., McGurl et al., 1994, *Proc. Natl. Acad. Sci. USA* 91(21):9799–9802; McGarvey et al., 1995, *Biotechnology* 13(13):1484–1487).

Seedlings are evaluated using plant germination, growth conditions and light sources described previously (McNellis et al., 1994b) and as discussed above. Protein immunoblot analysis is performed as described previously (McNellis et al., 1994a) and as set forth above in the Materials and Methods.

Transformed tomato seedlings contain both the wildtype TCOP1 gene and the transgene coding for the Coil domain Arabidopsis protein. The transgenic plants do not develop open, expanded leaves when grown in darkness. Furthermore, the transgenic tomato seedlings have shorter, more vigorous stems and greener, more developed leaves when compared to non-transformed Big Boy tomato seedlings grown under the same low light conditions. When grown to maturity under the same environmental conditions, the transgenic and non-transgenic (i.e., wildtype) tomato plants are not significantly different for total above-ground shoot growth or for yield of tomato fruits (botanically a berry).

Example 10

Production of Transformed Tomato Plants Using Conventional Plant Breeding

The transgenic Big Boy tomato plants produced in Example 9 are sexually crossed to non-transgenic Big Boy tomato plants (or another line, cultivar or variety of tomato plants) and the resultant seed is harvested. The harvested seed is planted and the seedlings are grown initially under darkness and then later under low light conditions and selection is made for transformed seedlings. The transformed seedlings are grown to maturity and the resultant selfed seed is harvested and bulked to produce bulked transgenic seed for planting as a tomato crop plant.

Alternatively, the mature transformed plants are crossed to a different tomato line (a sister line or a different variety) to produce hybrid seed. The resultant hybrid seed is bulked and used to produce a hybrid tomato crop.

As discussed above in the Materials and Methods, numerous variations on these breeding schemes are possible. For example, the originally obtained transformed seedlings may be selfed for one or several generations before being used for the production of either selfed or hybrid seed production. For a discussion of tomato production methods, see Langer et al., 1991, Agricultural Plants, Second Edition, Cambridge University Press.

Example 11

Production of Stably Transformed Transgenic Rice Lines Using the Coil Domain Sequence As discussed above, Tsuge et al. (1998) have established that rice plants inherently contain a homologue of the Arabidopsis COP1 gene.

The Arabidopsis Coil domain expression construct is ligated as HindIII fragments into the binary plant transformation vector pBIN19 as set forth in the Materials and Methods. Rice plants (*Oryza sativa* cv. Taipei 309) are transformed with the resultant vector according to published procedures (see, e.g., McElroy et al., 1991, *Plant Cell* 3(11):1155–1165; Nakayama et al., 1995, *Plant Mol. Biol.* 27(1):17–26; Su et al., 1998, *Plant Physiol.* 117(3):913–922; Cornejo et al., 1993, *Plant Mol. Biol.* 23(3):567–581; Xu et al., 1993, *Plant Mol. Biol.* 22(4):573–588).

Seedlings are evaluated using plant germination, growth conditions and light sources described previously (McNellis et al., 1994b) and as discussed herein. Protein immunoblot analysis is performed as described previously (McNellis et al., 1994a) and as set forth above in the Materials and Methods.

Transformed rice seedlings contain both the wildtype rice COP1 gene and the transgene coding for the Coil domain Arabidopsis protein. The transgenic plants do not develop open, expanded leaves when grown in darkness. Furthermore, the transgenic rice seedlings have shorter, more vigorous stems and greener, more developed leaves when compared to non-transformed rice seedlings grown under the same low light conditions. When grown to maturity under the same environmental conditions, the transgenic and non-transgenic (i.e., wildtype) rice plants are not significantly different for total above-ground shoot growth or for grain yield.

Example 12

Production of Transformed Rice Plants Using Conventional Plant Breeding

The transgenic rice plants produced in Example 11 are sexually crossed to non-transgenic rice plants (or another line, cultivar or variety of rice plants) and the resultant seed is harvested. The harvested seed is planted and the seedlings are grown first in darkness and then under low light conditions and selection is made for transformed seedlings. The transformed seedlings are grown to maturity and the resultant selfed seed is harvested and bulked to produce bulked transgenic seed for planting as a rice crop plant.

Alternatively, the mature transformed plants are crossed to a different rice line (a sister line or a different variety) to produce hybrid seed. The resultant hybrid seed is bulked and used to produce a hybrid rice crop.

As discussed above in the Materials and Methods, numerous variations on these breeding schemes are possible. For example, the originally obtained transformed seedlings may be selfed for one or several generations before being used for the production of either selfed or hybrid seed production. For a discussion of rice production methods, see Langer et al., 1991, Agricultural Plants, Second Edition, Cambridge University Press and Coffman et al., 1980, Chapter 36, In Hybridization of Crop Plants, The American Society of Agronomy, Inc., Madison, Wis.

Example 13

Production of Stably Transformed Transgenic Tomato Lines Using the Coil Domain of the TCOP1 Gene As discussed above, Frances et al. (1998) have cloned from tomato a homologue of the Arabidopsis COP1 gene, designated TCOP1. The Coil domain amino acids of the TCOP1 gene is introduced into a vector according to the methods described herein. The resultant vector is used to produce transformed tomato plants which are characterized and/or used as set forth in Examples 9 and 10.

Example 14

Production of Stably Transformed Transgenic Rice Lines Using the N-terminal Sequence of the Rice COP1 Gene As discussed above, Tsuge et al. (1998) have cloned from rice a homologue of the Arabidopsis COP1 gene. The Coil domain amino acids of the rice COP1 gene is introduced into a vector according to the methods described herein. The resultant vector is used to produce transformed rice plants which are characterized and/or used as set forth in Examples 11 and 12.

Example 15

Production of Transformed Arabidopsis Plants Using the Coil Domain of COP1, HY5 and GFP.

This example involves the analysis of Coil domain localization in transformed Arabidopsis cells using fusions of the Coil domain of COP1 and HY5 to an exemplary marker gene, the green fluorescent protein (GFP). HY5, a bZIP protein and positive regulator of photomorphogenic development, is described by Ang et al. (1998).

Applicable constructs, vectors and transformation processes for producing transgenic Arabidopsis cells are set forth above. Further guidance more specific to constructs containing GFP coding sequences can be found in U.S. Pat. Nos. 5,783,393 and 5,783,431, both incorporated by reference herein.

Transient expression assays of Arabidopsis cells will demonstrate the cellular targeting of a fusion protein consisting of the Coil domain and HY5 joined to GFP. By fluorescence microscopy and subcellular fractionations, the cellular locations of the fusion proteins can be determined.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

All references, articles, texts and patents referred to above and below are hereby incorporated by reference in their entirety.

Ahmnad, M. and Cashmore, A. R. (1993). The HY4 gene involved in blue light sensing in *Arabidopsis thaliana* encodes a protein with the characteristics of a blue light photoreceptor. *Nature* 366, 162–166.

Ang, L.-H. and Deng, X.-W. (1994). Regulatory hierarchy of photomorphogenic loci: allele-specific and light-dependent interaction between the HY5 and COP1 loci. *Plant Cell* 6, 613–628.

Ang, L.-H., Chattoadhyay, S., Wei, N., Oyama, T., Okada, K., Batshauer, A. and Deng, X.-W. (1998) Molecular interaction between COP1 and HY5 defines a regulatory switch for light control of seedling development. *Molecular Cell*, 1, 213–222.

Ausubel, F. M., Brent, R., Kingston, R. E., Moore, D. D., Seidman, J. G., Smith, J. A., and Struhl, K. eds (1994). *Saccharomyces cerevisiae* In Current Protocols in Molecular Biology, Supplement. (New York: John Wiley & Sons).

Bechtold, N., Ellis, J. and Pelletier, G. (1993) In planta Agrobacterium mediated gene transfer by infiltration of adult *Arabidopsis thaliana* plants. *C. R. Acad. Sci. Ser. III Sci. vi.*, 316, 1194–1199.

Bellon, S. F., Rodgers K. K., Schatz, D. G., Coleman, J. E. and Steitz, T. A. (1997) Crystal structure of the RAG1 dimerization domain reveals multiple zinc-binding motifs including a novel zinc binuclear cluster. *Nature Struc. Biol.*, 4, 586–591.

Berg, J. and Shi, Y. (1996) The galvanization of biology: a growing appreciation for the roles of zinc. *Science*, 271, 1081–1085.

Bevan, M. (1984). Binary Agrobacterium vectors for plant transformation. *Nucl. Acids Res.* 12, 8711–8721.

Borden, K. L. B. and Freemont, P. S. (1996) The Ring-finger domain: a recent example of a sequence-structure family. *Current Opinion Struc. Biol.* 6, 395–401.

Boylan, M. T., and Quail, P. H. (1991). Phytochrome A overexpression inhibits hypocotyl elongation in transgenic Arabidopsis. *Proc. Natl. Acad. Sci. USA* 88, 10806–10810.

Cao, H., Bowling S. A., Gordon, A. S., and Dong, X. (1994). Characterization of an Arabidopsis mutant that is nonresponsive to inducers of systemic acquired resistance. *Plant Cell* 6, 1583–1592.

Castle, L. A. and Meinke, D. W. (1994). A FUSCA gene of Arabidopsis encodes a novel protein essential for plant development. *Plant Cell* 6, 25–41.

Chamovitz, D. A., Wei, N., Osterlund, M. T., von Arnim, A. G., Staub, J. M., Matui, M. and Deng, X.-W. (1996) The Arabidopsis COP9 complex, a novel multisubunit nuclear regulator involved in light control of a developmental switch. *Cell*, 86, 115–121.

Chen, D.-C., Yang, B.-C., and Kuo, T.-T. (1992). One-step transformation of yeast in stationary phase. *Curr. Genet.* 21, 83–84.

Chen, Z., Silva, H., and Klessig, D. F. (1993). Active oxygen species in the induction of plant systemic acquired resistance by salicylic acid. *Science* 262, 1883–1886.

Chory, J. (1992) A genetic model for light-regulated seedling development in Arabidopsis. *Development*, 115, 337–354.

Chory, J. (1993) Out of darkness-mutants reveal pathways controlling light-regulated development in plants. *Trends. Genet.*, 9, 167–172.

Chory, J. and Li, J. (1997) Gibberellins, brassinosteroids and light-regulated development. *Plant, Cell and Environ.*, 20, 801–806.

Dehesh, K., Franci, C., Parks, B. M., Seeley, K. A., Short, T. W., Tepperman, J. M. and Quail, P. H. (1993). Arabidopsis HY8 locus encodes phytochrome A. *Plant Cell* 5, 1081–1088.

Deng, X.-W., Caspar, T., and Quail, P. H. (1991). cop1: A regulatory locus involved in light-controlled development and gene expression in Arabidopsis. *Genes Dev.* 5, 1172–1182.

Deng, X.-W. and Quail, P. H. (1992a). Genetic and phenotypic characterization of cop1 mutants of *Arabidopsis thaliana. Plant J.* 2, 83–95.

Deng, X.-W., Matsui, M., Wei, N., Wagner, D., Chu, A. M., Feldmann, K. A. and Quail, P. H. (1992b). COP1, an Arabidopsis regulatory gene, encodes a protein with both a zinc-binding motif and a $G_\beta$ homologous domain. *Cell* 71, 791–801.

Frances, S., White, M. J., Edgerton, M. D., Jones, A. M., Elliott, R. C. and Thompson, W. F. (1992). Initial characterization of a pea mutant with light-independent photomorphogenesis. *The Plant Cell* 4(12), 1519–130.

Frances, S., Matsui, M., Kendrick, R.E., and Deng, X.-W. A tomato homologue of the Arabidopsis COP1 gene exhibits a novel pattern of expression. ESOP Programme and Abstracts. European Symposium on Photomorhogenesis, Jul. 12–18, 1997.

Furuya, M. (1 993). *Annu. Rev. Plant Physiol. Plant Mol. Biol.* 44, 617–645.

Gilmartin, P. M., Sarokin, L., Memelink, J., and Chua, N.-H. (1990). *Plant Cell* 2, 369–378.

Green, R., and Fluhr, R. (1995). UV-B-induced PR-1 accumulation is mediated by active oxygen species. *Plant Cell* 7, 203–212.

Guarente, L. (1983). Yeast promoters and lacZ fusions designed to study expression of cloned genes in yeast. *Methods Enzymol.* 101, 181–191.

Gutjahr, T., Frei, E., Spicer, C., Baumgartner, S., White, R. A. H. and Noll M. (1 995) The Polycomb-group gene, extra sex combs, encodes a nuclear member of the WD-40 repeat family *EMBO J.*, 14, 4296–4306.

Gyuris, J., Golemis, E., Chertkov, H., and Brent, R. (1993). Cdi1, a human G1 and S phase protein phosphatase that associates with Cdk2. *Cell* 75, 791–803.

Hajdukiewics, P., Svab, Z. and Maliga, P. (1994) The small, versatile pPZP family of Agrobacterium binary vectors for plant transformation. *Plant Mol. Biol.,* 25, 989–994.

Hou, Y., von Arnim, A. G. and Deng, X.-W. (1993). A new class of Arabidopsis constitutive photomorphogenic genes involved in regulating cotyledon development. *Plant Cell* 5, 329–339.

Jefferson, R. A., Burgess, S. M. and Bevan, M. W. (1987) GUS fusions: β-glucuronidase as a sensitive and versatile gene fusion marker in higher plants. *EMBO J.,* 6, 3901–3907.

Kaufman, L. (1993). *Plant Physiol.* 102, 333–337.

Keleher, C., Redd, M. J., Schultz, J., Carlson, M. and Johnson, A. D. (1992) Ssn6-Tup1 is a general repressor of transcription in yeast. *Cell,* 68, 709–719.

Kendrick, R. E. and Kronenberg, G. H. M. (1994). Photomorphogenesis in plants. (Dordrecht: Kluwer Academic Publishers).

Komachi, K., Redd, M. J. and Johnson, A. D. (1994) The WD repeats of Tup1 interact with the homeo domain protein α2. *Genes Dev.,* 8, 2857–2867.

Koornneef, M., Rolff, E. and Spruit, C. J. P. (1980). Genetic control of light-inhibited hypocotyl elongation in *Arabidopsis thaliana* (L.) Heynh. *Z. Pflanzenphvsiol.* 100, 147–160.

Kraepiel, Y. and Miginiac, E. (1997) Photomorphogenesis and phytohromones. *Plant, Cell and Environ.,* 20, 807–812.

Kuras, L. and Thomas, D. (1995) Functional analysis of Met4p, a yeast transcriptional activator responsive to S-adenosylmethionine. *Mol. Cell Biol.,* 15, 208–216.

Kuras, L., Cherest, H., Surdin Kerjan, Y. and Thomas, D. (1996) A heteromeric complex containing the centromere binding factor1 and two basic leucine zipper factors, Met4 and Met28, mediates the transcriptional activation of yeast sulfer metabolism. *EMBO J.,* 15, 2519–2529.

Kwok, S. F., Piekos, B., Miséra, S., and Deng, X.-W. (1996) A complement often essential and pleiotropic Arabidopsis genes are necessary for suppression of photomorphogenesis in darkness. *Plant Physiol.* 110, 731–742.

Lin, C.-T., Ahmad, M., Gordon, D., and Cashmore, A. R. (1995). Expression of an Arabidopsis cryptochrome gene in transgenic tobacco results in hypersensitivity to blue, UV-A, and green light. *Proc. Natl. Acad. Sci. USA* 92, 8423–8427.

Lupas, A. (1996) Coiled coils: new structure and new functions. *TIBS,* 21, 375–382.

McCormac, A. C., Cherry, J. R., Hershey, H. P., Vierstra, R. D., and Smith, H. (1991). Photoresponses of transgenic tobacco plants expressing an oat phytochrome gene. *Planta* 185, 162–170.

McCormac, A. C., Whitelam, G. C., Boylan, M. T., Quail, P. H., and Smith, H. (1992). Light-grown plants of transgenic tobacco expressing an introduced oat phytochrome A gene under the control of a constitutive viral promoter exhibit persistent growth inhibition by far-red light. *Planta* 188, 173–181.

McCormac, A. C., Wagner, D., Boylan, M. T., Quail, P. H., Smith, H., and Whitelam, G. C. (1993). Photoresponses of transgenic Arabidopsis seedlings expressing introduced phytochrome B-encoding cDNAs: Evidence that phytochrome A and phytochrome B have distinct photoregulatory functions. *Plant J.* 4, 19–27.

McNellis, T. W., and Deng, X.-W. (1995). Light control of seedling morphogenetic pattern. *Plant Cell* 7, 1749–1761.

McNellis, T. W., von Arnim, A. G., Araki, T., Komeda, Y., Miséra, S. and Deng, X.-W. (1994a). Genetic and molecular analysis of an allelic series of cop1 mutants suggests functional roles for the multiple protein domains. *Plant Cell* 6, 487–500.

McNellis, T. W., von Arnim, A. G., and Deng, X.-W. (1 994b). Overexpression of Arabidopsis COP1 results in partial suppression of light mediated development: evidence for a light-inactivable repressor of photomorphogenesis. *Plant Cell* 6, 1391–1400.

McNellis, T. W., Torii, K. U. and Deng, X.-W. (1996). Expression of an N-terminal fragment of COP1 confers a dominant-negative effect on light-regulated seedling development in Arabidopsis. *Plant Cell,* 8, 1491–1503.

Matsui, M., Stoop, C. D., von Arnim, A. G., Wei, N. and Deng, X.-W. (1995) Arabidopsis COP1 protein specifically interacts in vitro with a cytoskeleton-associated protein, CIP1. *Proc. Natl. Acad. Sci. USA,* 92, 4239–4243.

Miséra, S., Müller, A. J., Weiland-Heidecker, U. and J ürgens, G. (1994). The FUSCA genes of Arabidopsis: Negative regulators of light responses. *Mol. Gen. Genet.* 244, 242–252.

Nagatani, A., Reed, R. W. and Chory, J. (1993). Isolation and initial characterization of Arabidopsis mutants that are deficient in phytochrome A. *Plant Physiol.* 102, 269–277.

Neer, E. J., Schmidt, C. J., Nambudripad, R. and Smith, T. F. (1994) The ancient regulatory-protein family of WD 40-repeat proteins. *Nature,* 371, 297–300.

Oyama, T., Shimula, Y. and Okada, K. (1997) The Arabidopsis HY5 gene encodes a bZIP protein that regulates stimulus-induced development of root and hypocotyl. *Genes Dev.,* 11, 2983–2995.

Parks, B. M. and Quail, P. H. (1993). hy8, a new class of Arabidopsis long hypocotyl mutants deficient in functional phytochrome A. *Plant Cell* 5, 39–48.

Pepper, A., Delaney, T., Washburn, T., Pool, D., and Chory, J. (1994). DET1, a negative regulator of light-mediated development and gene expression in Arabidopsis encodes a novel nuclear-localized protein. *Cell* 78, 109–116.

Quail, P. H. (1991). *Annu. Rev. Genet.* 25, 389–409.

Reed, J. M., Nagpal, P., Poole, D. S., Furuya, M. and Chory, J. (1993). Mutations in the gene for the red/far red light receptor phytochrome B alter cell elongation and physiological responses throughout Arabidopsis development. *Plant Cell* 5, 147–157.

Restreppo, M. A., Freed, D. D., and Carrington, J. C. (1990). Nuclear transport of plant potyviral proteins. *Plant Cell* 2, 987–998.

Saurin, A. J., Borden, K. L. B., Boddy, M. N. and Freemont, P. S. (1996) Does this have a familiar RING? *TIBS,* 21, 208–214.

Sherwood, P. W., Tsang, S. V.-M. and Osley, M. (1993) Characterization of HIR1 and HIR2, two genes required for regulation of histone gene transcription in *Saccharomyces cerevisiae*. *Mol. Cell Biol.*, 13, 28–38.

Spector, M. S., Raff, A., DeSilva, H., Lee, K. and Osley, M. A. (1997) Hir1p and Hir2p function as transcriptional corepressors to regulate histone gene transcription in the *Saccharomyces cerevisiae* cell cycle. *Mol. Cell. Biol.*, 17, 545–552.

Staub, J. M., Wei, N. and Deng, X.-W (1 996) Evidence for FUS6 as a component of the nuclear-localized COP9 complex in Arabidopsis. *Plant Cell,* 8, 2047–2056.

Thomas, D., Kuras, L., Barbey, B., Cherest, H., Blaiseau, P.-L. and Surdin-Kerjan, Y. (1995) Met30p, a yeast transcriptional inhibitor that responds to S-adenosylmethionine, is an essential protein with WD40 repeats. *Mol. Cell Biol.*, 15, 6526–6534.

Thompson, W. F., and White, M. J. (1991). *Annu. Rev. Plant Physiol. Plant Mol. Biol.* 42, 423–466.

Tomohiko, T. Yoshizumi, T., Deng, X.-W., and Matsui, M. 1997. Isolation and characterization of Arabidopsis COP1 homologous gene in rice. ESOP Programme and Abstracts. European Symposium on Photomorhogenesis, Jul. 12–18, 1997.

Torii, K. U., Mitsukawa, N., Oosumi, T., Matsuura, Y., Yokoyama, R., Whittier, R. F., and Komeda, Y. (1996). The Arabidopsis ERECTA gene encodes a putative receptor protein kinase with extracellular leucine-rich repeats. *Plant Cell* 8, 735–746.

Tzamarias, D. and Struhl, K. (1995) Distinct TPR motifs of Cyc8 are involved in recruiting the Cyc8-Tup1 corepressor complex to differentially regulated promoters. *Gene Dev,* 9, 821–831.

Uknes, S., Mauch-Mani, B., Moyer, M., Potter, S., Williams, S., Dincher, S., Chandler, D., Slusarenko, A., Ward, E., and Ryals J. (1992). Acquired resistance in Arabidopsis. *Plant Cell* 4, 645–656.

Vierstra, R. (1993). *Plant Physiol.* 103, 679–684.

von Arnim, A. G., and Deng, X.-W. (1993). Ring-finger motif of *Arabidopsis thaliana* COP1 defines a new class of zinc-binding domain. *J. Biol. Chem.* 268, 19626–19631.

von Arnim, A. G. and Deng, X.-W. (1994). Light inactivation of Arabidopsis photomorphogenic COP1 involves a cell-specific regulation of its nucleo-cytoplasmic partitioning. *Cell* 79, 1035–1045.

von Arnim, A. G., Osterlund, M. T., Kwok, S. F. and Deng, X.-W. (1997) Genetic and developmental control of nuclear accumulation of COP1, a repressor of photomorphogenesis in Arabidopsis. *Plant Physiol.,* 114, 779–788.

Wagner, D., Hoecker, U. and Quail, P. H. (1997) Red1 is necessary for phytochrome B-mediated red light-specific signal transduction in Arabidopsis. *Plant Cell* , 9, 731–743.

Wagner, D., Teppermann, J. M., and Quail, P. H. (1991). Overexpression of phytochrome B induces a short hypocotyl phenotype in transgenic Arabidopsis. *Plant Cell* 3, 1275–1288.

Wei, N., Chamovitz, D. A., and Deng, X.-W. (1994) Arabidopsis COP9 is a component of a novel signaling complex mediating light control of development. *Cell* 78, 117–124.

Wei, N. and Deng, X.-W. (1996) The role of the COP/DET/FUS genes in light control of Arabidopsis seedling development. *Plant Physiol.,* 112, 871–878.

Wei, N. and Deng, X.-W. (1998) Characterization and purification of the mammalian COP9 complex, a conserved nuclear regulator. *Phtochem. Photobio.* 68:237–241.

Wei, N., Tsuge, T., Serino, G., Dohmae, N., Takio, K., Matsui, M., and Deng, X.-W. (1998) The COP9 Complex is conserved between higher plants and mammals and is structurally related to the 26S Proteasome Regulatory Complex. *Current Biology.* 8:919–922.

Wester, L., Somers, D. E., Clack, T., and Sharrock, R. A. (1994). Transgenic complementation of the hy3 phytochrome B mutation and response to PHYB gene copy number in Arabidopsis. *Plant J.* 5, 261–272.

Whitelam, G. C., McCormac, A. C., Boylan, M. T., and Quail, P. H. (1992). Photoresponses of Arabidopsis seedlings expressing an introduced oat phyA cDNA: persistence of etiolated plant type responses in light-grown plants. *Photochem. Photobiol.* 56, 617–621.

Whitelam, G. C., Johnson, E., Peng, J., Carol, P., Anderson, M. L., Cowl, J. S. and Harberd, N. P. (1993). Phytochrome A null mutants of Arabidopsis display a wildtype phenotype in white light. *Plant Cell* 5, 757–768.

Yamamoto, Y. Y., Matsui, M., Ang, L. H. and X. W. Deng (1998) The role of a COP1 interactive protein in mediating light-regulated gene expression in Arabidopsis. *Plant Cell.* 10: 1083–1094.

Zhao, L., W. Chunxia, Y. Zhu, J. Zhao, and Wu, X. (1998). Molecular cloning and sequencing of the cDNA of cop1 gene from *Pisum sativum. Biochimica et Biophysica Acta* 1395, 326–328.

Zhou, D.-X., Kim, Y.-J., Li, Y.-F., Carol, P. and Mache, R. (1998) COP1b, an isoform of COP1 generated by alternative splicing, has a negative effect on COP1 function in regulating light-dependent seedling development in Arabidopsis. *Mol. Gen. Genet.,* 257, 387–391.

What is claimed is:

1. A transgenic plant cell comprising an endogenous COP1 gene and further comprising a nucleotide sequence encoding a separate and additional COP1 gene comprising a nucleotide sequence encoding a Coil domain, but which additional COP1 gene does not comprise nucleotide sequences encoding a ring finger domain or a WD-40 domain.

2. The plant cell of claim 1 wherein the nucleotide sequence coding for the Coil domain of the additional COP1 gene is SEQ ID NO:3.

3. The plant cell of claim 1 wherein the nucleotide sequence coding for the Coil domain of the additional COP1 gene is the nucleotide sequence which encodes SEQ ID NO:4.

4. The plant cell of claim 1 wherein the nucleotide sequence coding for the Coil domain of the additional COP1 gene consists of bases which encode amino acids at positions 128 to 209 of SEQ ID NO:2.

5. The plant cell of claim 1 wherein the nucleotide sequence coding for the Coil domain of the additional COP1 gene consists of bases which encode amino acids at positions 1–38 and 104–282 of SEQ ID NO:2.

6. A plant comprising one or more plant cells selected from the group consisting of the plant cells of claims 1, 2, 3, 4 and 5.

7. A purified and isolated DNA molecule comprising a nucleotide sequence encoding the Coil domain of COP1 or functionally equivalent fragments thereof, wherein said isolated DNA molecule does not encode a ring-finger or WD-40 domain of full-length COP-1 protein and wherein said functionally equivalent fragments thereof possess the ability to produce a seedling phenotype that exhibits: 1) compact, unexpanded leaves during seedling growth in extremely low light or complete darkness; and 2) shorter, more vigorous stems and greener, more developed leaves when compared to wildtype seedlings lacking an additional specific sequence coding for a Coil domain protein when grown under low light conditions.

8. A chemically synthesized DNA molecule comprising a nucleotide sequence encoding the Coil domain of COP1 or functionally equivalent fragments thereof, wherein said chemically synthesized DNA molecule does not encode a ring-finger or WD-40 domain of full-length COP-1 protein and wherein said functionally equivalent fragments thereof possess the ability to produce a seedling phenotype that exhibits: 1) compact, unexpanded leaves during seedling growth in extremely low light or complete darkness; and 2) shorter, more vigorous stems and greener, more developed leaves when compared to wildtype seedlings lacking an additional specific sequence coding for a Coil domain protein when grown under low light conditions.

9. A vector comprising the DNA molecule of claim 7 or claim 8.

10. A vector of claim 9, wherein said vector further comprises a promoter operably linked to said isolated DNA molecule.

11. A host cell transformed with the vector of claim 9 wherein the host cell is selected from the group consisting of prokaryotic cells, fungal cells and photosynthetic eukaryotic cells.

12. The photosynthetic eukaryotic host cells of claim 11 wherein the photosynthetic eukaryotic host is selected from the group consisting of monocotyledonous and dicotyledonous plants.

13. The photosynthetic eukaryotic host cells of claim 11 wherein the photosynthetic eukaryotic host is selected from the group consisting of Arabidopsis, spinach, tomato, pea and rice.

14. A purified and isolated DNA molecule of claim 7, wherein said DNA molecule is genomic DNA.

15. A purified and isolated DNA molecule of claim 7, wherein said DNA molecule is cDNA.

16. A vector comprising the DNA molecule of claim 14 or 15.

17. A vector of claim 16, wherein said vector further comprises a promoter operably linked to said isolated DNA molecule.

18. A host cell transformed with the vector of claim 16, wherein said host cell is selected from the group consisting of prokaryotic cells, fungal cells and photosynthetic eukaryotic cells.

19. A photosynthetic eukaryotic host cell of claim 18, wherein said eukaryotic host is selected from the group consisting of Arabidopsis, spinach, tomato, pea and rice.

20. A photosynthetic eukaryotic host cell of claim 18, wherein said photosynthetic eukaryotic host is selected from the group consisting of monocotyledonous and dicotyledonous plants.

21. A purified and isolated RNA molecule comprising a nucleotide sequence encoding the Coil domain of COP-1 or functionally equivalent fragments thereof, wherein said purified and isolated RNA molecule does not encode a ring-finger or WD-40 domain of full-length COP-1 protein and wherein said functionally equivalent fragments thereof possess the ability to produce a seedling phenotype that exhibits: 1) compact, unexpanded leaves during seedling growth in extremely low light or complete darkness; and 2) shorter, more vigorous stems and greener, more developed leaves when compared to wildtype seedlings lacking an additional specific sequence coding for a Coil domain protein when grown under low light conditions.

22. A chemically synthesized RNA molecule comprising a nucleotide sequence encoding the Coil domain of COP1 or functionally equivalent fragments thereof, wherein said chemically synthesized RNA molecule does not encode a ring-finger or WD-40 domain of full-length COP-1 protein and wherein said functionally equivalent fragments thereof possess the ability to produce a seedling phenotype that exhibits: 1) compact, unexpanded leaves during seedling growth in extremely low light or complete darkness; and 2) shorter, more vigorous stems and greener, more developed leaves when compared to wildtype seedlings lacking an additional specific sequence coding for a Coil domain protein when grown under low light conditions.

23. A method of modifying the normal function of the endogenous wildtype COP1 gene, wherein the method comprises:

a. preparing vectors comprising a nucleotide sequence coding for the Coil domain of the COP1 gene, wherein the vector does not contain a separate expressible nucleotide sequence coding for either a Ring-finger domain of the COP1 gene or for a WD-40 domain of the COP1 gene associated with said Coil domain nucleotide sequence; and b. inserting the vectors into cells selected from the group consisting of prokaryotic cells, fungal cells and photosynthetic eukaryotic cells to produce transformed cells.

24. The vectors of claim 23 wherein said vectors further comprise a promoter operably linked to said nucleotide sequence.

25. A purified and isolated DNA molecule consisting of the sequence of SEQ ID NO:3.

26. An isolated nucleic acid molecule which hybridizes under stringent conditions to SEQ ID NO:3, wherein said nucleic acid molecule does not comprise nucleotide sequences encoding a ring-finger domain or a WD-40 domain of the COP1 protein and wherein said nucleic acid molecule encodes a Coil domain protein.

27. A method of altering seedling emergence and growth characteristics by introducing into a plant cell a DNA molecule comprising a nucleotide sequence encoding the Coil domain of COP1 or functionally equivalent fragments thereof, but which DNA molecule does not comprise nucleotide sequences encoding a ring-finger domain or a WD-40 domain, wherein said method produces a seedling phenotype that exhibits: 1) compact, unexpanded leaves during seedling growth in extremely low light or complete darkness; and 2) shorter, more vigorous stems and greener, more developed leaves when compared to wildtype seedlings lacking an additional, specific sequence coding for a Coil domain protein when grown under low light conditions.

28. A method of altering seedling emergence and seedling growth characteristics by introducing into a plant cell a RNA molecule comprising a nucleotide seuence encoding the Coil domain of COP1 or functionally equivalent fragments thereof, but which RNA molecule does not comprise nucleotide sequences encoding a ring-finger domain or a WD-40 domain, wherein said method produces a seedling phenotype that exhibits: 1) compact, unexpanded leaves during seedling growth in extremely low light or complete darkness; and 2) shorter, more vigorous stems and greener, more developed leaves when compared to wildtype seedlings lacking an additional, specific sequence coding for a Coil domain protein when grown under low light conditions.

* * * * *

SEQUENCE LISTING

<160> NUMBER OF SEQ ID NOS: 11

<210> SEQ ID NO 1
<211> LENGTH: 888
<212> TYPE: DNA
<213> ORGANISM: Arabidopsis thaliana
<220> FEATURE:
<221> NAME/KEY: CDS
<222> LOCATION: (43)..(888)
<223> OTHER INFORMATION: N282 region of COP1 gene

<400> SEQUENCE: 1

```
caaaaaccaa aatcacaatc gaagaaatct tttgaaagca aa atg gaa gag att        54
                                                Met Glu Glu Ile
                                                  1 tcg acg gat ccg gtt gtt cca gcg gtg aaa cct gac ccg aga aca tct      102
Ser Thr Asp Pro Val Val Pro Ala Val Lys Pro Asp Pro Arg Thr Ser
  5              10                  15                  20 tca gtt ggt gaa ggt gct aat cgt cat gaa aat gac gac gga gga agc      150
Ser Val Gly Glu Gly Ala Asn Arg His Glu Asn Asp Asp Gly Gly Ser
             25                  30                  35 ggc ggt tct gag att gga gca ccg gat ctg gat aaa gac ttg ctt tgt      198
Gly Gly Ser Glu Ile Gly Ala Pro Asp Leu Asp Lys Asp Leu Leu Cys
         40                  45                  50 ccg att tgt atg cag att att aaa gat gct ttc ctc acg gct tgt ggt      246
Pro Ile Cys Met Gln Ile Ile Lys Asp Ala Phe Leu Thr Ala Cys Gly
     55                  60                  65 cat agt ttc tgc tat atg tgt atc atc aca cat ctt agg aac aag agt      294
His Ser Phe Cys Tyr Met Cys Ile Ile Thr His Leu Arg Asn Lys Ser
 70                  75                  80 gat tgt ccc tgt tgt agc caa cac ctc acc aat aat cag ctt tac cct      342
Asp Cys Pro Cys Cys Ser Gln His Leu Thr Asn Asn Gln Leu Tyr Pro
 85                  90                  95                 100 aat ttc ttg ctc gat aag cta ttg aag aaa act tca gct cgg cat gtg      390
Asn Phe Leu Leu Asp Lys Leu Leu Lys Lys Thr Ser Ala Arg His Val
            105                 110                 115 tca aaa act gca tcg ccc ttg gat cag ttt cgg gaa gca cta caa agg      438
Ser Lys Thr Ala Ser Pro Leu Asp Gln Phe Arg Glu Ala Leu Gln Arg
        120                 125                 130 ggt tgt gat gtg tca att aag gag gtt gat aat ctt ctg aca ctt ctt      486
Gly Cys Asp Val Ser Ile Lys Glu Val Asp Asn Leu Leu Thr Leu Leu
    135                 140                 145 gcg gaa agg aag aga aaa atg gaa cag gaa gaa gct gag agg aac atg      534
Ala Glu Arg Lys Arg Lys Met Glu Gln Glu Glu Ala Glu Arg Asn Met
150                 155                 160 cag ata ctt ttg gac ttt ttg cat tgt cta agg aag caa aaa gtt gat      582
Gln Ile Leu Leu Asp Phe Leu His Cys Leu Arg Lys Gln Lys Val Asp
165                 170                 175                 180 gaa cta aat gag gtg caa act gat ctc cag tat att aaa gaa gat ata      630
Glu Leu Asn Glu Val Gln Thr Asp Leu Gln Tyr Ile Lys Glu Asp Ile
                185                 190                 195 aat gcc gtt gag aga cat aga ata gat tta tac cga gct agg gac aga      678
Asn Ala Val Glu Arg His Arg Ile Asp Leu Tyr Arg Ala Arg Asp Arg
            200                 205                 210 tat tct gta aag ttg cgg atg ctc gga gat gat cca agc aca aga aat      726
Tyr Ser Val Lys Leu Arg Met Leu Gly Asp Asp Pro Ser Thr Arg Asn
        215                 220                 225 gca tgg cca cat gag aag aac cag att ggt ttc aac tcc aat tct ctc      774
Ala Trp Pro His Glu Lys Asn Gln Ile Gly Phe Asn Ser Asn Ser Leu
    230                 235                 240 agc ata aga gga gga aat ttt gta ggc aat tat caa aac aaa aag gta      822
Ser Ile Arg Gly Gly Asn Phe Val Gly Asn Tyr Gln Asn Lys Lys Val
245                 250                 255                 260 gag ggg aag gca caa gga agc tct cat ggg cta cca aag aag gat gcg      870
Glu Gly Lys Ala Gln Gly Ser Ser His Gly Leu Pro Lys Lys Asp Ala
                265                 270                 275 ctg agt ggg tca gat tcg                                              888
Leu Ser Gly Ser Asp Ser
            280

<210> SEQ ID NO 2
```

-continued

```
<211> LENGTH: 282
<212> TYPE: PRT
<213> ORGANISM: Arabidopsis thaliana

<400> SEQUENCE: 2

Met Glu Glu Ile Ser Thr Asp Pro Val Val Pro Ala Val Lys Pro Asp
 1               5                  10                  15

Pro Arg Thr Ser Ser Val Gly Glu Gly Ala Asn Arg His Glu Asn Asp
            20                  25                  30

Asp Gly Gly Ser Gly Gly Ser Glu Ile Gly Ala Pro Asp Leu Asp Lys
        35                  40                  45

Asp Leu Leu Cys Pro Ile Cys Met Gln Ile Ile Lys Asp Ala Phe Leu
 50                  55                  60

Thr Ala Cys Gly His Ser Phe Cys Tyr Met Cys Ile Ile Thr His Leu
 65                  70                  75                  80

Arg Asn Lys Ser Asp Cys Pro Cys Cys Ser Gln His Leu Thr Asn Asn
                85                  90                  95

Gln Leu Tyr Pro Asn Phe Leu Leu Asp Lys Leu Leu Lys Lys Thr Ser
            100                 105                 110

Ala Arg His Val Ser Lys Thr Ala Ser Pro Leu Asp Gln Phe Arg Glu
        115                 120                 125

Ala Leu Gln Arg Gly Cys Asp Val Ser Ile Lys Glu Val Asp Asn Leu
130                 135                 140

Leu Thr Leu Leu Ala Glu Arg Lys Arg Lys Met Glu Gln Glu Glu Ala
145                 150                 155                 160

Glu Arg Asn Met Gln Ile Leu Leu Asp Phe Leu His Cys Leu Arg Lys
                165                 170                 175

Gln Lys Val Asp Glu Leu Asn Glu Val Gln Thr Asp Leu Gln Tyr Ile
            180                 185                 190

Lys Glu Asp Ile Asn Ala Val Glu Arg His Arg Ile Asp Leu Tyr Arg
        195                 200                 205

Ala Arg Asp Arg Tyr Ser Val Lys Leu Arg Met Leu Gly Asp Asp Pro
210                 215                 220

Ser Thr Arg Asn Ala Trp Pro His Glu Lys Asn Gln Ile Gly Phe Asn
225                 230                 235                 240

Ser Asn Ser Leu Ser Ile Arg Gly Gly Asn Phe Val Gly Asn Tyr Gln
                245                 250                 255

Asn Lys Lys Val Glu Gly Lys Ala Gln Gly Ser Ser His Gly Leu Pro
            260                 265                 270

Lys Lys Asp Ala Leu Ser Gly Ser Asp Ser
        275                 280

<210> SEQ ID NO 3
<211> LENGTH: 246
<212> TYPE: DNA
<213> ORGANISM: Arabidopsis thaliana
<220> FEATURE:
<221> NAME/KEY: CDS
<222> LOCATION: (1)..(246)
<223> OTHER INFORMATION: Coil domain of N282 region of COP1 gene

<400> SEQUENCE: 3 gaa gca cta caa agg ggt tgt gat gtg tca att aag gag gtt gat aat     48
Glu Ala Leu Gln Arg Gly Cys Asp Val Ser Ile Lys Glu Val Asp Asn
 1               5                  10                  15 ctt ctg aca ctt ctt gcg gaa agg aag aga aaa atg gaa cag gaa gaa     96
Leu Leu Thr Leu Leu Ala Glu Arg Lys Arg Lys Met Glu Gln Glu Glu
            20                  25                  30
```

```
gct gag agg aac atg cag ata ctt ttg gac ttt ttg cat tgt cta agg      144
Ala Glu Arg Asn Met Gln Ile Leu Leu Asp Phe Leu His Cys Leu Arg
         35                  40                  45 aag caa aaa gtt gat gaa cta aat gag gtg caa act gat ctc cag tat      192
Lys Gln Lys Val Asp Glu Leu Asn Glu Val Gln Thr Asp Leu Gln Tyr
 50                  55                  60 att aaa gaa gat ata aat gcc gtt gag aga cat aga ata gat tta tac      240
Ile Lys Glu Asp Ile Asn Ala Val Glu Arg His Arg Ile Asp Leu Tyr
 65                  70                  75                  80 cga gct                                                              246
Arg Ala <210> SEQ ID NO 4
<211> LENGTH: 82
<212> TYPE: PRT
<213> ORGANISM: Arabidopsis thaliana

<400> SEQUENCE: 4

Glu Ala Leu Gln Arg Gly Cys Asp Val Ser Ile Lys Glu Val Asp Asn
 1               5                  10                  15

Leu Leu Thr Leu Leu Ala Glu Arg Lys Arg Lys Met Glu Gln Glu Glu
             20                  25                  30

Ala Glu Arg Asn Met Gln Ile Leu Leu Asp Phe Leu His Cys Leu Arg
         35                  40                  45

Lys Gln Lys Val Asp Glu Leu Asn Glu Val Gln Thr Asp Leu Gln Tyr
 50                  55                  60

Ile Lys Glu Asp Ile Asn Ala Val Glu Arg His Arg Ile Asp Leu Tyr
 65                  70                  75                  80

Arg Ala

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer for
      cloning

<400> SEQUENCE: 5
ccgctcgagc cgaaactgat ccaagggcga                                      30

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Primer for
      cloning

<400> SEQUENCE: 6
ccgctcgaga agttgcggat gctcggaga                                       29

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence:
      PCR primer

<400> SEQUENCE: 7
acgcgtcgac cccaaactga tccaagggcg a                                    31
```

```
<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:  PCR primer

<400> SEQUENCE: 8
catgccatgg ataagctatt gaagaaaact                                          30

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:  PCR primer

<400> SEQUENCE: 9
ccgctcgagt tagtccctag ctcggtataa atc                                      33

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:  PCR primer

<400> SEQUENCE: 10
catgccatgg ttggtgaagg tgctaatcgt                                          30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:  PCR primer

<400> SEQUENCE: 11
ccgctcgagt tatgacacat gccgagctga                                          30
```